United States Patent
Seki et al.

(10) Patent No.: US 7,998,543 B2
(45) Date of Patent: Aug. 16, 2011

(54) DIOXETANE COMPOUND, CATIONICALLY POLYMERIZABLE COMPOSITION, OPTICAL FILM, AND LIQUID CRYSTAL DISPLAY DEVICE

(75) Inventors: Takashi Seki, Yokohama (JP); Takeshi Kataoka, Yokohama (JP); Hitoshi Mazaki, Yokohama (JP); Hirofumi Aizono, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 538 days.

(21) Appl. No.: 12/281,008

(22) PCT Filed: Oct. 17, 2006

(86) PCT No.: PCT/JP2006/320994
§ 371 (c)(1),
(2), (4) Date: Aug. 28, 2008

(87) PCT Pub. No.: WO2007/099669
PCT Pub. Date: Sep. 7, 2007

(65) Prior Publication Data
US 2009/0068379 A1   Mar. 12, 2009

(30) Foreign Application Priority Data
Feb. 28, 2006 (JP) .................................. 2006-053652

(51) Int. Cl.
| C09K 19/38 | (2006.01) |
| C09K 19/34 | (2006.01) |
| C09K 19/20 | (2006.01) |
| C09K 19/30 | (2006.01) |
| C07D 305/06 | (2006.01) |
| C07D 407/10 | (2006.01) |
| C07D 407/12 | (2006.01) |
| C08G 65/18 | (2006.01) |

(52) U.S. Cl. ............... 428/1.1; 252/299.61; 252/299.63; 252/299.67; 549/510; 549/511; 522/168; 525/410

(58) Field of Classification Search .................... 428/1.1; 252/299.61, 299.63, 299.67; 525/410; 522/168; 549/510, 511
See application file for complete search history.

(56) References Cited

U.S. PATENT DOCUMENTS

| 5,064,697 A | 11/1991 | Takiguchi et al. |
| 5,193,020 A | 3/1993 | Shiozaki et al. |
| 5,413,657 A | 5/1995 | Yamanashi et al. |
| 5,773,178 A | 6/1998 | Shiota et al. |
| 6,139,772 A | 10/2000 | Ukon |
| 6,183,822 B1 | 2/2001 | Farrand et al. |
| 6,210,872 B1 | 4/2001 | Hosaki et al. |
| 6,660,344 B2 | 12/2003 | Lub |
| 6,666,989 B1 | 12/2003 | Toyne et al. |
| 6,894,141 B2 | 5/2005 | Satoh et al. |
| 7,087,273 B2 | 8/2006 | Matsumoto et al. |
| 7,763,182 B2 * | 7/2010 | Seki et al. .................. 252/299.6 |
| 2002/0054262 A1 | 5/2002 | Kitagawa et al. |
| 2003/0072893 A1 | 4/2003 | Nakano et al. |
| 2003/0090617 A1 | 5/2003 | Kawamoto et al. |
| 2005/0101752 A1 | 5/2005 | Matsumoto et al. |
| 2009/0208673 A1 | 8/2009 | Seki et al. |

FOREIGN PATENT DOCUMENTS

| EP | 0528050 A1 | 2/1993 |
| EP | 0896047 A1 | 2/1999 |
| EP | 1428823 A1 | 6/2004 |
| EP | 1 469 058 A1 | 10/2004 |
| JP | 3-9326 A | 1/1991 |
| JP | 03-239788 A | 10/1991 |
| JP | 4-57017 A | 2/1992 |
| JP | 5-333313 A | 12/1993 |
| JP | 06-020434 A | 1/1994 |
| JP | 08-278491 A | 10/1996 |
| JP | 09-003454 A | 1/1997 |
| JP | 09-073081 A | 3/1997 |
| JP | 11-080081 A | 3/1999 |
| JP | 11-106380 A | 4/1999 |
| JP | 11-158258 A | 6/1999 |
| JP | 2000-321426 A | 11/2000 |
| JP | 2001-049205 A | 2/2001 |
| JP | 2002-146353 A | 5/2002 |
| JP | 2002-308832 A | 10/2002 |
| JP | 2003-139953 A | 5/2003 |
| JP | 2003-213265 A | 7/2003 |
| JP | 2004-123597 A | 4/2004 |
| JP | 2004-123882 A | 4/2004 |
| JP | 2004-510785 A | 4/2004 |
| JP | 2004-315736 A | 11/2004 |
| JP | 2006-028428 A | 2/2006 |
| WO | 02/28985 A1 | 4/2002 |
| WO | WO 2007116573 A1 * | 10/2007 |

OTHER PUBLICATIONS

European Supplemental Search Report issued on May 11, 2010 in European Application No. EP 06 81 2114.
Office Action issued Sep. 16, 2004 in U.S. Appl. No. 10/801,459.
Office Action issued May 23, 2005 in U.S. Appl. No. 10/801,459.
Office Action issued Sep. 14, 2005 in U.S. Appl. No. 10/801,459.
Office Action issued Aug. 30, 2005 in U.S. Appl. No. 10/801,459.

* cited by examiner

*Primary Examiner* — Shean C Wu
(74) *Attorney, Agent, or Firm* — Panitch Schwarze Belisario & Nadel LLP

(57) ABSTRACT

A novel dioxetane compound is provided having a cationically polymerizable oxetane group, which compound is excellent in compatibility with a liquid crystalline compound and a non-liquid crystalline compound. An optical film is also provided with excellent liquid crystal orientation retention properties and mechanical strength, produced by aligning a composition of the dioxetane compound and a cationically polymerizable compound in a liquid crystal orientation and fixing the liquid crystal orientation by polymerization. Further, a liquid crystal display device is provided with the optical film.

13 Claims, 10 Drawing Sheets

DIOXETANE COMPOUND, CATIONICALLY POLYMERIZABLE COMPOSITION, OPTICAL FILM, AND LIQUID CRYSTAL DISPLAY DEVICE

CROSS-REFERENCE TO RELATED APPLICATIONS

This application is a Section 371 of International Application No. PCT/JP2006/320994, filed Oct. 17, 2006, which was published in the Japanese language on Sep. 7, 2007, under International Publication No. WO 2007/099669 A1 and the disclosure of which is incorporated herein by reference.

BACKGROUND OF THE INVENTION

The present invention relates to novel dioxetane compounds, cationically polymerizable compositions containing such dioxetane compounds, optical films produced from such polymerizable compositions, and liquid crystal display devices equipped with such optical films.

In recent years, active studies and developments have been carried out so as to utilize liquid crystalline compounds as optical materials, and many of them have been already put into practical use. In order to apply a liquid crystalline compound as an optical material, it is essential that after the molecules of the compound are aligned and fixed in a liquid crystal state, the aligned state can be retained under practical use conditions. As methods for retaining a liquid crystalline compound in an aligned state, there have been proposed various methods such as those using polymerizable liquid crystalline compounds, polymeric liquid crystalline compounds, polymeric liquid crystalline compounds having crosslinkable reactive groups, and the combination of polymeric liquid crystalline compounds having crosslinkable reactive groups and polymerizable liquid crystalline compounds.

As a method using polymeric liquid crystalline compounds having crosslinkable reactive groups, there has been proposed a method using a polymerizable liquid crystalline compound having a mesogen portion comprising two or more benzene rings or similar rings, spacer portions each comprising a hydrocarbon chain, and a radically polymerizable reactive group such as a (meth)acrylate group at one or both of the terminal ends (Patent Document No. 1). In this method, such a polymerizable liquid crystalline compound is coated in a heat-melted state or in the form of a solution on an alignment substrate and dried if necessary so as to be formed into a liquid crystalline layer. Thereafter, the liquid crystalline layer thus formed is aligned in a liquid crystal state by heating and then polymerized by photo-irradiation so as to fix the layer in the liquid crystal state. However, it is necessary for this method to suppress undesired polymerization inhibition effects caused by oxygen in the air and conduct some complicated operations such as photo-irradiation under an inert gas atmosphere, requiring improvements in facilities and apparatus. Since a (meth)acrylate group is apt to polymerize with light or heat, a careful attention must be paid during the synthesis.

A liquid crystalline compound is known which contains a cationically polymerizable group in place of a (meth)acrylic group, both groups of which have an symmetrical structure viewed from the mesogen group and have characteristics that they have liquid crystallinity (Patent Document Nos. 2 and 3).

As the method using a polymeric liquid crystalline compound, it is proposed to use a liquid crystalline polyester with excellent properties to be retained in the liquid crystal orientation (Patent Document No. 4). However, as a result of the widespread of mobile devices, an optical film comprised of such a liquid crystalline polyester has been demanded to have properties to retain the liquid crystal orientation under more sever practical use conditions and more excellent mechanical strength as well.

As the method using a polymeric liquid crystalline compound having a polymerizable reactive group, there has been proposed a method wherein a polymerizable reactive group is introduced into the polymeric main chain and a method wherein a monomer unit having a polymerizable reactive group is introduced into a side chain. However, since in either of these methods, the liquid crystallinity of the material used is decreased, there is a limit to the amount of the polymerizable group to be introduced to enhance the sufficient mechanical strength. Therefore, alternative methods have been demanded (Patent Document No. 5).

As a method wherein a polymeric liquid crystalline compound having a crosslinkable reactive group is mixed with a polymerizable liquid crystalline compound, there has been proposed the use of a composition comprising a side chain type polymeric liquid crystalline compound having an oxetane group and a liquid crystalline dioxetane compound (Patent Document No. 6). This composition can be enhanced in mechanical strength by increasing the amount of the liquid crystalline dioxetane compound. However, it is necessary to add a compound that is capable of generating cations with light and/or heat in order to effect polymerization rapidly while the liquid crystal phase is retained. However, the liquid crystalline dioxetane compound is highly compatible with a liquid crystalline compound but can not be sufficient in compatibility with a non-liquid crystalline compound such as the foregoing compounds capable of generating cations because it is likely to cause phase separation when the non-liquid crystalline compound is added.

Patent Document No. 1: Japanese Patent Laid-Open Publication No. 11-080081
Patent Document No. 2: U.S. Pat. No. 5,773,178
Patent Document No. 3: Japanese Laid-Open PCT International publication No. 2004-510785
Patent Document No. 4: Japanese Patent Laid-Open Publication No. 11-158258
Patent Document No. 5: Japanese Patent Laid-Open Publication No. 9-3454
Patent Document No. 6: Japanese Patent Laid-Open Publication No. 2004-315736

BRIEF SUMMARY OF THE INVENTION

The present invention has an object to provide a compound which can overcome the foregoing problems, specifically which requires no complicated process carried out under an inert gas atmosphere or carried out to inhibit contact with air and contains no functional group such as (meth)acrylate or epoxy groups, the syntheses of which are difficult and further is excellent in compatibility with another compound regardless of whether the compound has liquid crystallinity or not; a cationically polymerizable composition containing such a compound; and an optical film containing such a compound.

As the result of extensive research and study of a cationically polymerizable compound which can be readily synthesized and is excellent in compatibility with various compounds, the inventors of the present invention found a dioxetane compound having cationically polymerizable groups as polymerizable groups and developed a new optical film with excellent retainability of the liquid crystal orientation after having been aligned and fixed therein and excellent mechanical strength on the basis of the finding that the dioxetane compound can be uniformly aligned without causing phase separation in a composition of the dioxetane compound and a cationically polymerizable compound and easily polymerized to be fixed in the aligned state and thus formed into a film.

That is, according to a first aspect of the present invention, there is provided a dioxetane compound represented by formula (1) below:

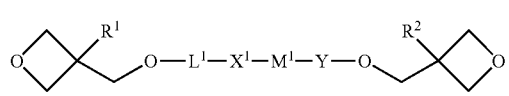

(1)

wherein $R^1$ and $R^2$ are each independently hydrogen, methyl, or ethyl, $L^1$ denotes —$(CH_2)_n$— wherein n is an integer of 1 to 12, $X^1$ denotes a single bond, —O—, —O—CO— or —CO—O—, Y denotes a single bond or —CO—, $M^1$ is represented by formula (2) or (3) below wherein $P^1$ and $P^3$ are each independently a group selected from the group consisting of those represented by formula (4) below, and $P^2$ is a group selected from the group consisting of those represented by formula (5) below, and $L^2$ and $L^3$ are each denotes a single bond, —CH=CH—, —C≡C—, —O—, —O—CO—, or —CO—O—:

(2)

(3)

(4)

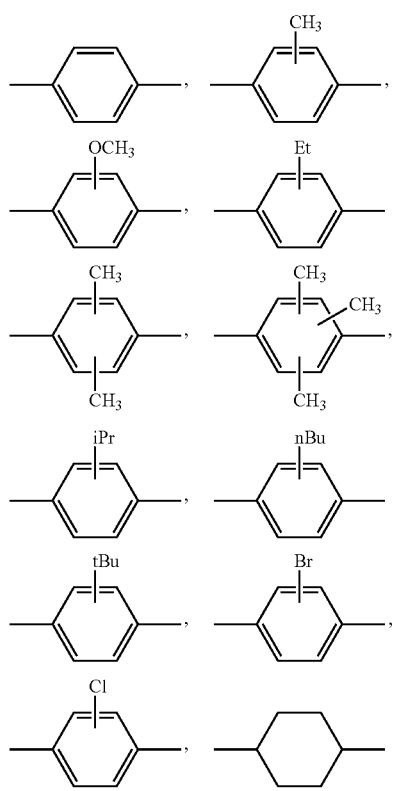

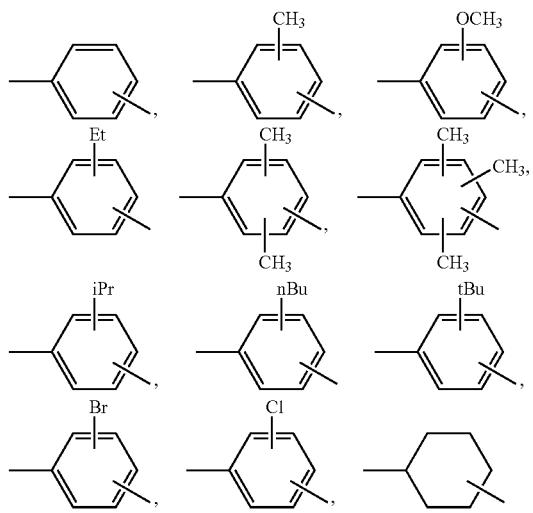

(5)

According to a second aspect of the present invention, there is provided the dioxetane compound according to the first aspect wherein in formula (1) $L^1$ is —$(CH_2)_2$—, —$(CH_2)_4$—, or —$(CH_2)_6$—, and Y is a single bond.

According to a third aspect of the present invention, there is provided a cationically polymerizable composition comprising a dioxetane compound represented by formula (1) and a compound having a cationically polymerizable group, provided that the compound represented by formula (1) is excluded.

According to a fourth aspect of the present invention, there is provided the cationically polymerizable composition according to the third aspect wherein the composition contains at least 5 percent by mass or more of a dioxetane compound represented by formula (1).

According to a fifth aspect of the present invention, there is provided the cationically polymerizable composition according to the third aspect wherein the compound having a cationically polymerizable group is a compound exhibiting liquid crystallinity.

According to a sixth aspect of the present invention, there is provided the cationically polymerizable composition according to the fifth aspect wherein the compound exhibiting liquid crystallinity is an oligomer or a polymer.

According to a seventh aspect of the present invention, there is provided the cationically polymerizable composition according to the third aspect wherein the composition contains a photo cation generator and/or a thermal cation generator.

According to a eighth aspect of the present invention, there is provided an optical film produced by polymerizing the cationically polymerizable composition according to any one of the third to seventh aspects.

According to a ninth aspect of the present invention, there is provided a liquid crystal display equipped with the optical film according to the eighth aspect.

The dioxetane compound of the present invention is a novel compound, and a composition comprising the dioxetane compound and a cationically polymerizable compound can be uniformly aligned in a liquid crystal state without causing phase separation and easily polymerized to be fixed in the liquid crystal state and formed into a film thereby rendering it possible to produce an optical film with excellent retainability of the liquid crystal orientation formed after having been aligned and fixed and excellent mechanical strength.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
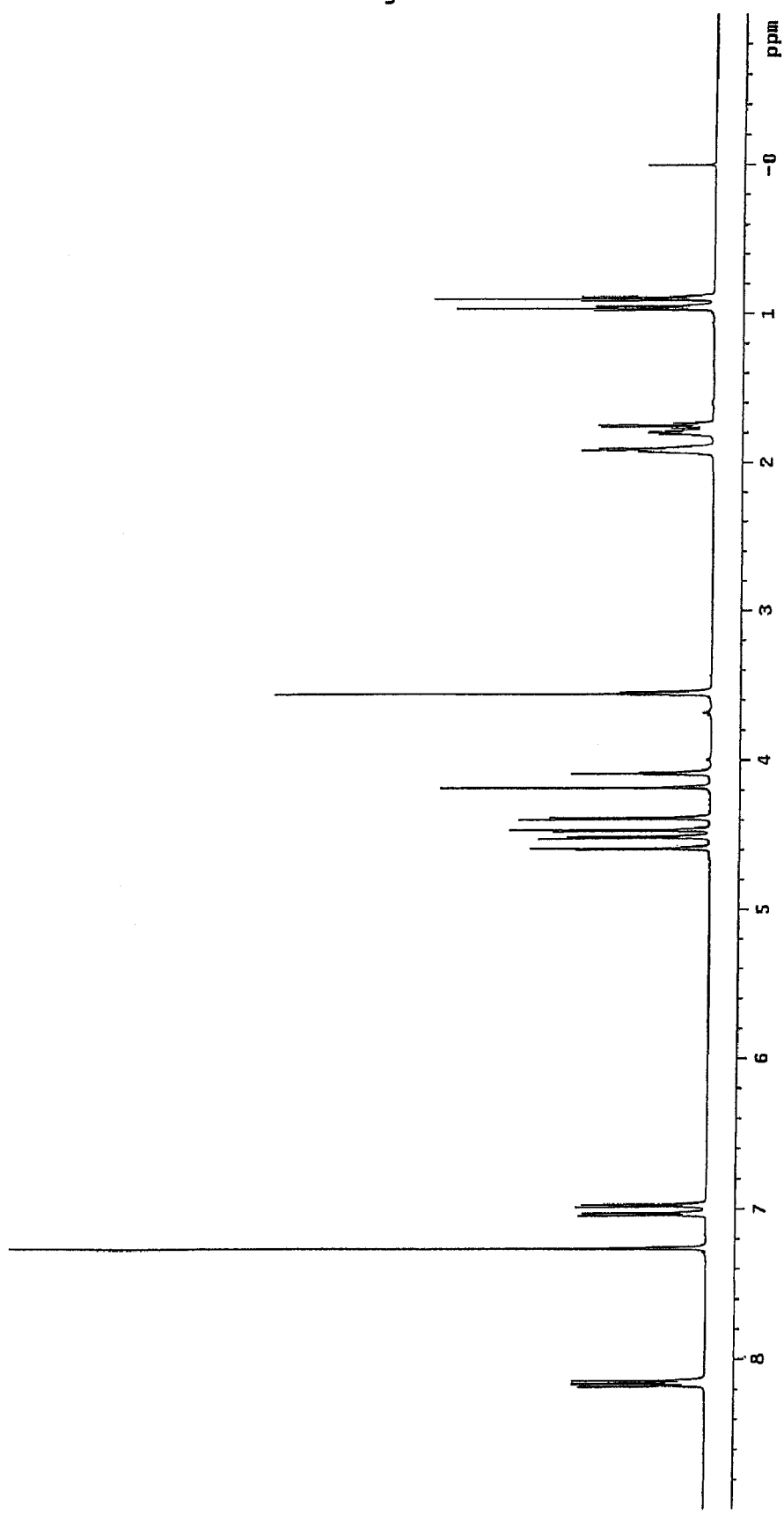
FIG. 1 is the $^1$NMR spectrum of dioxetane compound 1 synthesized in Example 1.

The present invention will be described hereinafter in more detail.

The dioxetane compound of the present invention is a compound represented by formula (1) below and has a remarkable feature that the interconnecting groups coupling the M$^1$ group to the oxetane groups positioned on the right and left sides thereof are different from one another (asymmetric). The compound represented by formula (1) with this structure does not exhibit liquid crystallinity irrespectively having the mesogen group "M$^1$":

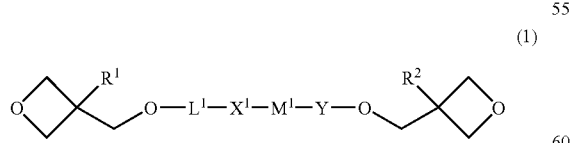

(1)

wherein R$^1$ and R$^2$ are each independently hydrogen, methyl, or ethyl, L$^1$ denotes —(CH$_2$)$_n$— wherein n is an integer of 1 to 12, X$^1$ denotes a single bond, —O—, —O—CO— or —CO—O—, Y denotes a single bond or —CO—, M$^1$ is represented by formula (2) or (3) below wherein P$^1$ and P$^3$ are each independently a group selected from the group consisting of those represented by formula (4) below, and P$^2$ is a group selected from the group consisting of those represented by formula (5) below, and L$^2$ and L$^3$ are each denotes a single bond, —CH═CH—, —C≡C—, —O—, —O—CO—, or —CO—O—:

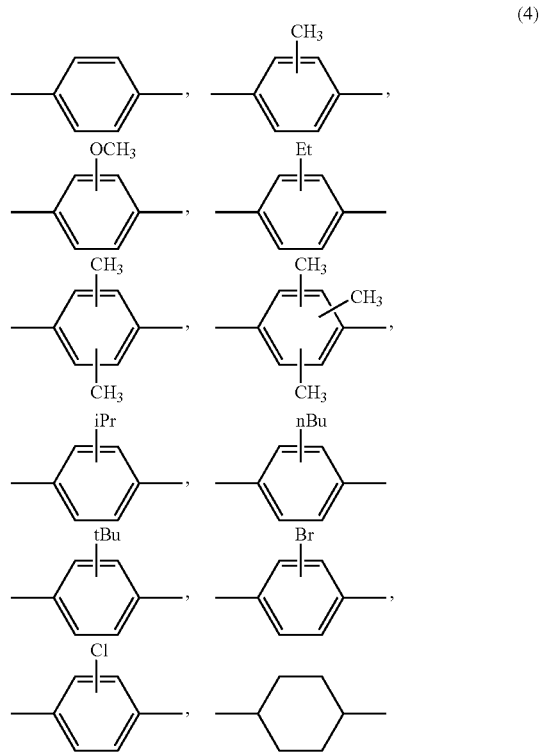

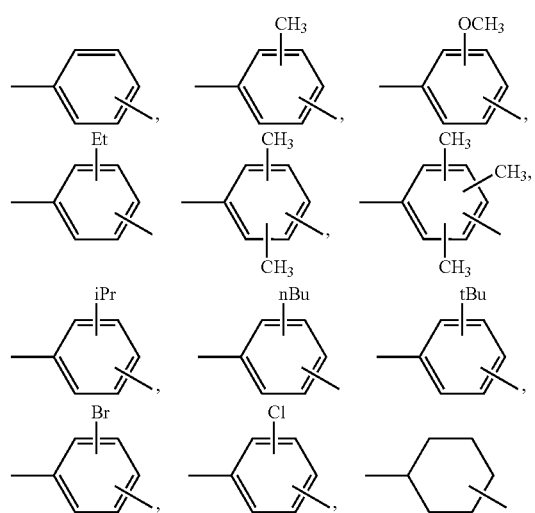

There are many compounds that can be exemplified as compounds represented by formula (1) because of variation in combination of L$^1$, X$^1$, Y and M$^1$. However, preferred examples include compounds wherein L$^1$ is —(CH$_2$)$_2$—, —(CH$_2$)$_4$— or —(CH$_2$)$_6$— and Y is a single bond. More specific examples include the following compounds:

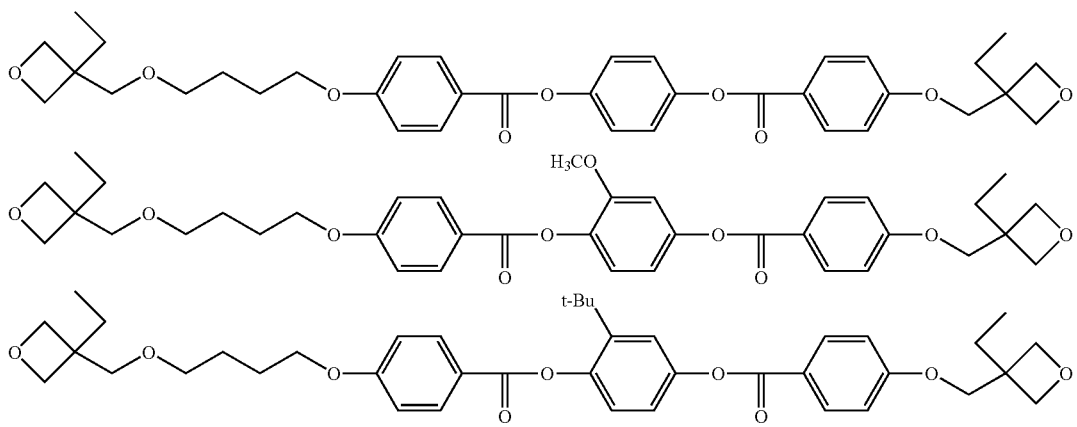

There is no particular restriction on the method of synthesizing the dioxetane compound represented by formula (1) of the present invention because it can be synthesized in accordance with any conventional method utilized in the field of organic chemistry.

During these syntheses, since the oxetane groups have cationic polymerizability, it is necessary to select the reaction conditions with a consideration given to side reactions such as polymerization and ring-opening possibly occurring under strong acid conditions. The oxetane groups are less potential to induce such side reactions, compared with oxylane group which is though a similar cationically polymerizable functional group. Furthermore, since the oxetane group may allow various compounds similar thereto, such as alcohols, phenols, and carboxylic acids to react with one another, the use of protection groups may be considered if necessary. The crude oxetane compound derivative thus synthesized may be refined by recrystallization or column chromatography. Recrystallization is effective particularly for compounds of a rather high crystallinity. Even if the compound can not be recrystallized at ordinary temperature, it may be able to be recrystallized after being cooled to a lower temperature of such as −20° C.

More specific examples of the synthesis methods include those wherein hydroxybenzoic acid as the starting material is bonded to oxetane groups with for example the Williamson ether synthesis and then the resulting compound is bonded to a diol suitable for the present invention with an acid chloride method or condensation with carbodiimide and wherein hydroxybenzoic acid is condensed with a diol suitable for the present invention after the hydroxyl group is protected with an appropriate protection group and then the hydroxyl group is reacted with a proper oxetane compound such as haloalkyloxetane after the protection group is desorbed.

Reaction between the oxetane compound and the hydroxyl group may be carried out under suitable conditions selected depending on the configuration or reactivity of the compounds to be used. Generally, the reaction temperature is from −20 to 180° C., preferably from 10 to 150° C. while the reaction time is from 10 minutes to 48 hours, preferably from 30 minutes to 24 hours. Ranges other than the foregoing ranges are not preferable because the reaction would not proceed sufficiently or a side reaction would occur. The mixing ratio of the oxetane compound and the hydroxyl group is preferably from 0.8 to 1.2 equivalent of oxetane compound per equivalent of hydroxyl group.

The reaction may be carried out without using a solvent but is usually carried out in the presence of a solvent. There is no particular restriction on the solvent as long as it does not bother the intended reaction. Examples of the solvent include aromatic hydrocarbons such as benzene, toluene and xylene; amides such as dimethylformamide, dimethylacetoamide and N-methylpyrorridone; ketones such as methyl ethyl ketone and methyl isobutyl ketone; ethers such as dibutyl ether, ethylene glycol dimethyl ether and diethylene glycol dimethyl ether; esters such as ethyl acetate and ethyl benzoate; and mixtures thereof.

The present invention also relates to a cationically polymerizable composition comprising the above-described dioxetane compound and a compound having a cationically polymerizable group (excluding the dioxetane compound of the present invention).

The cationically polymerizable composition is a composition comprising the dioxetane compound of the present invention and a compound having a cationically polymerizable group other than the dioxetane compound of the present invention and containing preferably at least 5 to 60 percent by mass, more preferably 10 to 50 percent by mass of the dioxetane compound. A content of the dioxetane compound of less than 5 percent by mass is not preferable because the concentration of the polymerizable group would be low and thus mechanical strength after polymerization would be insufficient. A content of the dioxetane compound of more than 60 percent by mass is not also preferable because the resulting composition would be likely to cause phase separation.

There is no particular restriction on the compound having a cationically polymerizable group to be blended with the dioxetane compound of the present invention as long as it is a compound having a cationically polymerizable group as represented by formula (6) below (excluding the dioxetane compound of the present invention) and can be mixed therewith. Therefore, examples of the compound having a cationically polymerizable group include various low molecular weight compounds, various polymeric compounds with an ability to be formed into a film and various low molecular weight liquid crystalline compounds and polymeric liquid crystalline compounds both exhibiting liquid crystallinity. Further, compounds having no cationically polymerizable group and various dyes, pigments and additives may be added to an extent that the achievement of the purposes of the present invention is not bothered. Among these, preferred are compounds exhibiting liquid crystallinity and the whole composition preferably exhibits liquid crystallinity for the production of an optical film described below.

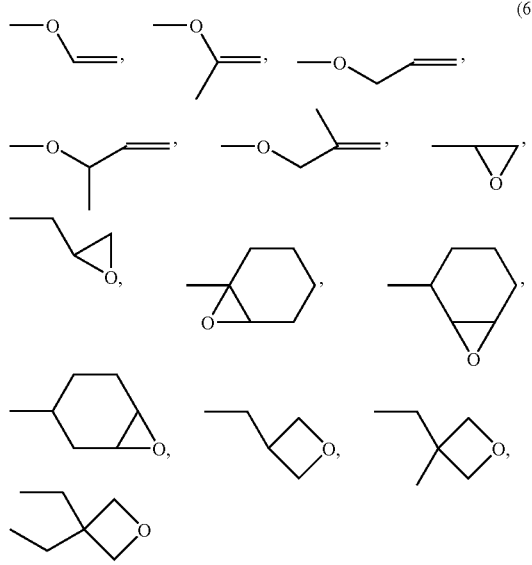

(6)

There are various compounds having a cationically polymerizable group and exhibiting liquid crystallinity. However, preferred are oligomers exhibiting liquid crystallinity and polymeric liquid crystalline compounds. The polymeric liquid crystalline compounds may be of main chain type or side chain type. Examples of the main chain type polymeric liquid crystalline compounds include polyesters, polyesteramides and polycarbonates. Examples of the side chain type liquid crystalline compounds include polyacrylates, polysiloxanes and polymalonates.

There is no particular restriction on the method of synthesizing the main chain type liquid crystalline polyester since there may be employed any method usually used for synthesizing polyesters. For example, there may be employed a method in which a carboxylic acid unit is activated in acid chloride or sulfonic acid anhydride and reacted with a phenol unit in the presence of a base (acid chloride method), in which a carboxylic acid unit and a phenol unit are directly condensed using a condensing agent such as DCC (dicyclohexylcarbodiimide), or in which a phenol unit is acetylated and deacetonation-polymerized, together with a carboxylic acid unit under a molten state. However, since in the case of using deacetonation-polymerization under a molten state, there is a risk that the monomer unit having a cationically polymerizable group undergoes polymerization or decomposition unexpectedly under the reaction conditions, there frequently arises a necessity to control the reaction conditions strictly. Furthermore, under particular circumstances, it may be desired to employ a method wherein a suitable protection group is used or wherein after a compound having a different functional group is brought into a reaction, a cationically polymerizable group is introduced. Alternatively, the crude main chain type liquid crystalline polyester produced by polymerization may be refined by recrystallization or reprecipitation.

The side chain type polymeric liquid crystalline compound may also be synthesized with various methods. For example, when a poly(meth)acrylate is synthesized, a liquid crystalline (meth)acrylic compound having a cationically polymerizable group at one of its terminal ends is radically or anionically polymerized to polymerize the (meth)acrylic group only thereby producing a side chain type polymeric liquid crystalline compound having a cationically polymerizable group.

As an example of radical polymerization, a method may be used in which a (meth)acrylic compound is dissolved in a solvent such as dimethylformamide (DMF) and reacted at a temperature of 60 to 10° C. for several hours using 2,2′-azobisisobutylonitrile (AIBN) or benzoyl peroxide (BPO) as an initiator. Alternatively, in order to allow the liquid crystal phase to be stably exhibited, there is an effective method in which living radical polymerization is carried out using an initiator such as a copper (I) bromide/2,2′-bipyridyl-based initiator or a 2,2,6,6-tetramethylpiperidinyloxy free radical (TEMPO)-based initiator so as to control the molecular weight distribution. These radical polymerizations are needed to be carried out strictly in the absence of oxygen.

As an example of the anionic polymerization, a method may be used in which a (meth)acrylic compound is dissolved in a solvent such as tetrahydrofuran (THF) and reacted using a strong base such as an organic lithium compound, an organic sodium compound or the Grignard reagent as an initiator. Alternatively, this polymerization can be converted to living anionic polymerization by optimizing the initiator or reaction temperature thereby controlling the molecular weight distribution. These anionic polymerizations are needed to be carried out strictly under dehydration and deoxidation conditions.

If necessary, another compound that can be copolymerized may be copolymerized. There is no particular restriction on compounds to be copolymerized. However, preferred are (meth)acrylic compounds having a mesogen group so as to enhance the liquid crystallinity of the polymeric compound to be synthesized.

There is no particular restriction on the method of synthesizing the (meth)acrylic compound having a cationically polymerizable group. Therefore, there may be used any conventional method utilized in the field of organic chemistry.

For example, a portion having a cationically polymerizable group is coupled to a portion having a (meth)acrylic group by means of the Williamson's ether synthesis or an ester synthesis using a condensing agent thereby synthesizing a (meth)acrylic compound having two completely different reactive functional groups, i.e., a cationically polymerizable group and a (meth)acrylic group.

Since the cationically polymerizable composition of the present invention comprises a compound having a cationically polymerizable group, a cation generator is preferably added thereto to polymerize (cure) the compounds.

There are cation generators such as photo cation generators capable of generating cations with appropriate light and thermal cation generators capable of generating cations with heat (hereinafter may be collectively referred to as "cation generator"). To the cationically polymerizable composition may be added these cation generators alone or in combination. If necessary, various sensitizing agents may be added.

More specifically described, the term "photo cation generator" used herein denotes a compound which can generate cations by irradiation of a light with a specific wavelength and may be any of organic sulfonium salt-, iodonium salt-, or phosphonium salt-based compounds. Counter ions of these compounds are preferably antimonate, phosphate, and borate. Specific examples include $Ar_3S^+SbF_6^-$, $Ar_3P^+BF_4^-$, and $Ar_2I^+PF_6^-$ wherein Ar indicates a phenyl or substituted phenyl group. Sulfonic acid esters, triazines, diazomethanes, β-ketosulfones, iminosulfonates, and benzoinsulfonates may also be used.

The term "thermal cation generator" used herein denotes a compound which can generate cations by heating to a certain temperature and may be any of benzylsulfonium salts, benzylammonium salts, benzylpyridinium salts, benzylphosphonium salts, hydrazinium salts, carbonic acid esters, sulfonic acid esters, amineimides, antimony pentachloride-acetyl chloride complexes, diaryliodonium salt-dibenzyloxy coppers, and halogenated boron-tertiary amine adducts.

There may be employed a method wherein a cationically polymerizable liquid crystalline composition having been blended with a compound generating cations, such as Lewis acid is prepared beforehand and then polymerized by allowing cations to generate after being coated or dried. When the cationically polymerizable composition exhibits liquid crystallinity, there may be employed a method wherein the cationically polymerizable groups are polymerized after or simultaneously with a liquid crystal orientation is formed. However, in a practical manner, it is more preferred to use a cation generator eliciting the generation of cations with heat or light because both sufficient liquid crystal orientation and polymerization degree can be achieved more frequently in the case where a liquid crystal orientation aligning process and a polymerization process are separated.

In the case of using a thermal cation generator, a heat treatment for aligning the polymerizable liquid crystalline composition is carried out at a temperature lower than the activation temperature of the thermal cation generator (the index thereof which is usually used is a 50% dissociation temperature), followed by a step of generating cations wherein a heat treatment is carried out at the activation temperature or higher to dissociate the thermal cation generator thereby reacting the cationically polymerizable groups with the cations thus generated. This method has an advantage that the aligning process and polymerization reaction can be conducted only in heat treatment facilities. However, this method has a disadvantage that since the aligning and polymerization processes are separated only with heat, i.e., difference in temperature, undesired polymerization may slightly progress during the aligning process or may not progress sufficiently during the actual polymerization process.

In the case of using a photo cation generator, the cationically polymerizable liquid crystalline composition can be aligned, maintaining sufficient fluidity without undergoing polymerization or decomposition during the aligning process if the heat treatment for aligning the composition in a liquid crystal orientation is carried out under such dark conditions that the photo cation generator is not dissociated. Thereafter, the polymerizable liquid crystalline composition may be allowed to polymerize, i.e., cure with a light irradiated from a light source capable of emitting an appropriate wavelength of light so as to generate cations.

Since the amount of the cation generator to be added to the cationically polymerizable liquid crystalline composition varies depending on the structures of compounds constituting the composition and various additives to be used, or the equivalent weight of the oxetane group, it can not be determined with certainty. However, it is within the range of usually 100 ppm to 30 percent, preferably 1,000 ppm to 25 percent, more preferably 0.2 percent to 20 percent, and most preferably 0.5 percent to 15 percent on the basis of the mass of the cationically polymerizable composition. An amount of the cation generator of less than 100 ppm is not preferable because polymerization may not progress due to the insufficient amount of cation to be generated. An amount of the cation generator of more than 30 percent is not also preferable because a large amount of the undecomposed residue of the cation generator is likely to remain and be colored and may cause the light resistance to degrade.

Among the above-described cation generators, the photo cation generators capable of generating cations with light are particularly preferable because they can generate cations and polymerize (cure) the polymerizable liquid crystalline composition at any temperature at which the composition exhibits a liquid crystal phase.

The cationically polymerizable composition is formed into a film and polymerized (cured) thereby producing an optical film.

Next, description will be given of a method of producing an optical film using the cationically polymerizable liquid crystalline composition of the present invention. Although not restricted, the method of producing an optical film preferably goes through each of the steps included in the method described below.

An optical film made from the cationically polymerizable liquid crystalline composition of the present invention may be in any form such as one wherein the optical film is kept on an alignment substrate, i.e., (alignment substrate/(alignment layer)/optical film); one wherein the optical film is transferred to a transparent substrate film other than an alignment substrate, i.e., (transparent substrate film/optical film); or one wherein the optical film is used as a single layer (optical film only) when it has a self-standing property.

Substrates which may be used in the present invention are preferably those that can align the composition of the present invention in a liquid crystal state also considering the case where the cationically polymerizable composition may exhibit liquid crystallinity. Examples of such substrates include films formed from polyimide, polyamide, polyamideimide, polyphenylene sulfide, polyphenylene oxide, polyether ketone, polyetherether ketone, polyether sulfone, polysulfone, polyethylene terephthalate, polyethylene naphthalate, polyarylate, triacetyl cellulose, epoxy resins, phenol resins, cycloolefin polymers, and uniaxially stretched films thereof. Some of these films exhibit a sufficient alignability for the cationically polymerizable composition of the present invention depending on the method of producing the films even though they are not subjected to an aligning treatment. However, if a film does not have alignability sufficiently or at all, the film may be stretched by an appropriate heating treatment; subjected to a rubbing treatment wherein the film is rubbed in one direction with a rayon cloth or the like or wherein the film is rubbed after a conventional alignment layer of polyimide, polyvinyl alcohol, or a silane coupling agent is formed over the film; subjected to an oblique vapor deposition with silicon oxide; or subjected to the combination of these treatments to be provided with alignability. Alternatively, the alignment substrate may be a metal plates of aluminum, iron, or copper or any of various glass plates on which surfaces fine grooves are regularly formed.

In the case where an alignment substrate is not optically isotropic or makes the resulting optical film opaque at a wavelength region where the film is intended to be used, the optical film may be transferred from such an alignment substrate to an optically isotropic film or a substrate which is transparent at a wavelength region where the optical film is intended to be used. Examples of the method of transferring include those as disclosed in Japanese Patent Laid-Open Publication Nos. 4-57017 and 5-333313 wherein after an optical film layer on an alignment substrate is laminated via a tacky adhesive or adhesive over a transparent substrate which is different from the alignment substrate and if necessary the adhesive is cured, only the optical film is transferred to the transparent substrate by releasing the alignment substrate from the laminate.

Examples of the transparent substrate onto which the liquid crystal layer is transferred include triacetyl cellulose films such as Fujitac (manufactured by Fuji Photo Film Co., Ltd.) and Konicatac (manufactured by Konica Corp.); TPX film (manufactured by Mitsui Chemical Inc.); Arton film (manufactured by JSR); Zeonex film (manufactured by Zeon Corp.); and Acryplene film (manufactured by Mitsubishi Rayon Co., Ltd.). If necessary, the transparent substrate may be a polarizer or a retardation film produced by stretching a polycarbonate, a cycloolefin polymer or a polyester. Alternatively, a quartz plate or a glass plate may be used. A polarizer may be used regardless of whether or not a protective layer is used.

There is no particular restriction on the tacky adhesive or adhesive to be used to transfer the optical film as long as it is of optical grade. Therefore, there may be used conventional acrylic-, epoxy resin-, ethylene-vinyl acetate copolymer-, rubber-, urethane-based adhesives, mixture types thereof, or various reactive adhesives of such as thermal curing type and/or photo curing type or electron radiation curing types.

The reaction (curing) conditions under which the reactive tacky adhesives or adhesives are cured vary depending on their formulation, viscosity and reaction temperature thereof. Therefore, the curing may be conducted under the conditions properly selected. For example, photo-curing type adhesives may be cured at a similar irradiation dose using a similar light source to those used for a photo cation generator described hereinafter. Electron radiation curing type adhesives may be cured at an accelerating voltage of usually 10 kV to 200 kV, preferably 25 kV to 100 kV.

The optical film may be produced by a method wherein a cationically polymerizable liquid crystalline composition in a molten state or in the form of a solution is coated over an alignment substrate. The coated layer on the alignment layer is dried and if necessary heated and/or stretched, and then subjected to a photo irradiation and/or a heat treatment (polymerization) thereby being formed into an optical film.

There is no particular restriction on the solvent used for preparing a solution of the cationically polymerizable liquid crystalline composition of the present invention as long as it can dissolve each component constituting the composition and be evaporated under appropriate conditions. Preferred examples of the solvent include ketones such as acetone, methyl ethyl ketone, and isophorone; ether alcohols such as butoxy ethyl alcohol, hexyloxy ethyl alcohol, and methoxy-2-propanol; glycol ethers such as ethylene glycol dimethyl-ether and diethylene glycol dimethyl ether; ester-based solvents such as ethyl acetate, methoxypropyl acetate and ethyl lactate; phenol-based solvents such as phenol and chlorophenol; amide-based solvents such as N,N-dimethylformamide, N,N-dimethylacetoamide, and N-methylpyrrolidone; halogenated hydrocarbon-based solvents such as chloroform, tetrachloroethane, and dichlorobenzene; and mixtures thereof. Surfactants, defoaming agents, or leveling agents may be added to the solution so as to form a uniform film layer on an alignment substrate. Furthermore, for the purpose of coloring, dichroic dyes, dyes, or pigments may be added to an extent that the exhibition of liquid crystallinity is not inhibited.

There is no particular restriction on the coating method as long as the uniformity of the film layer can be maintained. Therefore, there may be used any conventional method such as roll coating, die coating, dip coating, curtain coating, or spin coating methods. The coating may be followed by a solvent-removing process, i.e., drying using a heater or a hot air blowing.

The thickness of the coated film is adjusted depending on the physical properties of a cationically polymerizable composition (refractive index anisotropy, constituents) or the usage of the resulting optical film. The thickness of the coated film after being dried is from 0.1 to 20 μm, preferably 0.3 to 10 μm. When the cationically polymerizable composition has a refractive index anisotropy, the retardation (refractive index anisotropy×film thickness) is adjusted to be from 20 to 1000 nm, preferably 50 to 800 nm. The ranges deviating these ranges are not preferable because they make the exhibition of the intended effects difficult.

Heat treatment may be carried out if necessary before the coated film is subjected to a photo irradiation and/or a heat treatment to be polymerized (cured). This heat treatment is preferably incorporated when the cationically polymerizable composition exhibits liquid crystallinity. The polymerizable liquid crystalline composition used is heated to the range of temperatures at which the composition exhibits a liquid crystal phase, so as to align the composition in a liquid crystal state by its self-alignability. Since the conditions for the heat treatment vary in optimum conditions and limits depending on the liquid crystal phase behavior temperature (transition temperature) of the polymerizable liquid crystalline composition to be used, it can not be determined with certainty. However, the heat treatment is conducted at a temperature within the range of usually 10 to 250° C. and preferably 20 to 200° C. Too low temperatures are not preferable because there is a possibility that the composition may not be aligned in a liquid crystal state sufficiently, while too high temperatures are not also preferable because cationically polymerizable groups such as oxetane group or substrates may be adversely affected. The heat treatment is conducted for usually 3 seconds to 30 minutes, preferably 10 seconds to 10 minutes. The heat treatment for shorter than 3 seconds is not preferable because there is a possibility that the composition may not be aligned in a liquid crystal phase completely. Whereas, the heat treatment for longer than 30 minutes is not also preferable because the productivity is extremely deteriorated. After the liquid crystalline composition is completely aligned in a liquid crystal state by heat treatment or the like, the composition on the alignment substrate is cured by polymerization. In the present invention, the polymerization/curing process is carried out in order to modify the coated film by polymerization or curing reaction to fix the film in a liquid crystal state to be a harder film layer.

In the case of using a photo-cation generator, a light is irradiated from a light source capable of emitting an appropriate wavelength of light so as to allow the photo-cation generator to generate cations. The light irradiation is carried out with different optimum values such as irradiation wavelength, irradiation intensity or irradiation time depending on the type or amount of a photo-cation generator to be used but is usually carried out by irradiating a light from a light source having a spectrum in an absorption wavelength region of the photo-cation generator to be used, such as a metal halide lamp, a high-pressure mercury lamp, a low-pressure mercury lamp, a xenon lamp, an arc discharge lamp, a laser and a synchrotron irradiation light source thereby decomposing the photo-cation generator. The irradiation dose per cm is within the range of generally 1 to 2,000 mJ and preferably 10 to 1,000 mJ in the integrated irradiation dose. However, when the absorption region of the photo-cation generator is extremely different from the spectrum of the light source, or the cationically polymerizable composition itself can absorb a light in the wavelength of the light source, the irradiation dose is not limited to the foregoing range. In these cases, a method may be employed in which a suitable photo sensitizer or two or more types of photo-cation generators having different absorption wavelengths may be used.

The optical film produced through the above-described processes becomes a sufficiently solid and strong film. More specifically, since the three-dimensional bond of the mesogen portion is achieved by the curing reaction, the optical film layer is significantly improved not only in heat-resistance but also in mechanical strength such as resistance to scratch, wear, and cracking compared with that before being cured. The present invention is of great significance in the industrial sense because it can achieve an improvement in thermal/mechanical strength and also the precise control, i.e., liquid crystal orientation when the cationically polymerizable composition has liquid crystallinity, at the same time.

When the cationically polymerizable composition of the present invention has liquid crystallinity, its orientation structure can be controlled by selecting proper compounds to be added, if necessary, rendering it possible to produce an optical film with a fixed nematic, twisted nematic, cholesteric or nematic hybrid orientation. The optical film has many usages depending on its orientation structure.

For example, an optical film with a fixed nematic or twisted nematic orientation may be used as a compensation plate for a transmissive or reflection type of liquid crystal display device of STN, TN, OCB or HAN mode. Optical films with a fixed cholesteric orientation can be used as polarizing reflective films for luminance enhancement, reflection type color filters, and security elements or various decoration films utilizing color variations of reflection light depending on viewing angles peculiar to the selective reflection. Those with a fixed nematic hybrid orientation can be used as a viewing angle improving film for TN-type liquid crystal display devices utilizing a retardation upon viewing from the front or the asymmetric nature caused by the orientation of retardation value (inclination of the film). Furthermore, those having a function as a ¼ wavelength plate when used in combination with a polarizer can be used as anti-glare filters for reflection type liquid crystal displays and EL displays.

EXAMPLES

The present invention will be further described in the following examples, but the present invention should not be construed as being limited thereto.

The analyzing methods used in the examples are as follows.

(1) $^1$H-NMR and $^{13}$C-NMR Measurement

A compound was dissolved in deuterated chloroform or deuterated dimethylsulfoxide, and the $^1$H-NMR and $^{13}$C-NMR were determined with "INOVA 400" manufactured by VARIAN Co., Ltd.

(2) Observation of Liquid Crystal Phase Behavior

Liquid crystal phase behavior was observed using a polarizing microscope "Olympus BH2" while heating a sample on a hot stage "FP82HT" manufactured by Mettler-Toledo International Inc.

Phase transition temperature was measured using a differential scanning calorimeter "DSC7" manufactured by Perkin Elmer Co.

The DSC measurement conditions (under nitrogen flow) are as follows:

Step 1: the temperature is increased from 25° C. to 150° C. at a rate of 5° C./min;

Step 2: the temperature is decreased from 150° C. to 25° C. at a rate of 5° C./min; and Step 3: the temperature is increased from 25° C. to 200° C. at a rate of 5° C./min.

Peaks emerging in Steps 2 and 3 were determined as phase transition temperatures. The ordinate of each DSC chart indicates the calorie variation cause by phase change and upwardly projected peaks indicate endotherm. Regarding the description of phase behavior, "C" indicates crystal phase, "Ch" indicates cholesteric phase, "Nm" indicates nematic phase, and "Iso" indicates isotropic liquid phase. Further, for example, "C-Iso" indicates a phase change between "C" and "Iso".

(3) Parameter Measurement of Optical Film

The retardation (Δnd) of a nematic orientation was measured using "KOBRA-20ADH" manufactured by Oji Keisokukiki Co., Ltd. The measurement was carried out at a wavelength of 550 nm unless otherwise stated.

The average tilt angle of a nematic hybrid orientation was determined through a simulation wherein the tilt angle is assumed to change in a linear form, using Δnd from −50 to 50 degrees incremented by 10 degrees measured with "KOBRA-20ADH" manufactured by Oji Keisokukiki Co., Ltd.

The twisted angle and Δnd of a twisted nematic structure were measured using "Optipro" manufactured by SHIN-TECH, Inc.

(4) Measurement of Film Thickness

The thickness of a film was measured using SURFACE TEXTURE ANALYSIS SYSTEM Dektak 3030ST manufactured by SLOAN Co. A method was also used in which the film thickness was determined by interference measurement ("Ultraviolet Visible Near-Infrared Spectrophotometer V-570" manufactured by JASCO Corporation) and refractive index data.

(5) Measurement of GPC

GPC measurement was carried out by dissolving compounds in tetrahydrofuran and using 8020 GPC system manufactured by TOSOH CORPORATION equipped with TSK-GEL, Super H1000, Super H2000, Super H3000, and Super H4000 which are connected in series and tetrahydrofuran as an eluent solvent. Polystyrene was used as a standard for calibration of the molecular weight.

(6) Measurement of IR

IR was measured using "Genesis II FT-IR" manufactured by Mattson Instruments.

(7) Measurement of Transmission Spectrum

The measurement of transmission spectrum was carried out "Ultraviolet Visible Near-Infrared Spectrophotometer V-570" manufactured by JASCO Corporation.

The abbreviations used in schemes of reference examples and examples are as follows:

DCC: 1,3-dicyclohexylcarbodiimide
DMAP: 4-dimethylaminopyridine
DCM: dichloromethane
PPTS: pyridinium-p-toluene sulfonate
THF: tetrahydrofuran
DMF: dimethylformamide
BHT: 2,6-di-t-butyl-4-methylphenol
TEA: triethylamine
iPr: isopropyl Reference Example 1

Synthesis of Intermediate Compound 1 Having an Oxetanyl Group

In accordance with Scheme 1 below, an intermediate compound 1 having an oxetanyl group was synthesized using 3-ethyl-3-hydroxymethyloxetane (OXT-101, manufactured by Toagosei Co., Ltd.) as the raw material.

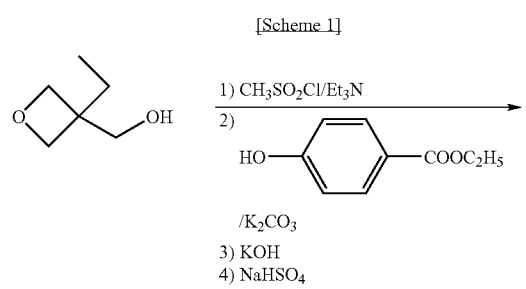

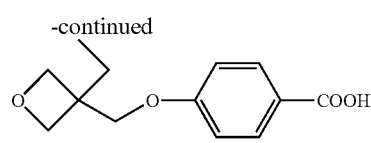

Intermediate Compound 1 having an oxetanyl group

Reference Example 2

Synthesis of Intermediate Compound 2 Having an Oxetanyl Group

In accordance with Scheme 2 below, an intermediate compound 2 having an oxetanyl group was synthesized.

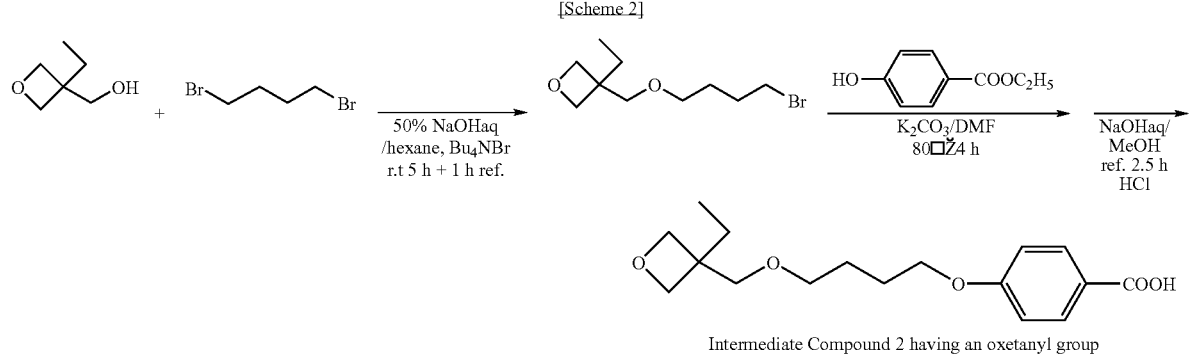

Intermediate Compound 2 having an oxetanyl group

Reference Example 3

Synthesis of Acrylic Compound 3

In accordance with Scheme 3 below, an acrylic compound 3 was synthesized.

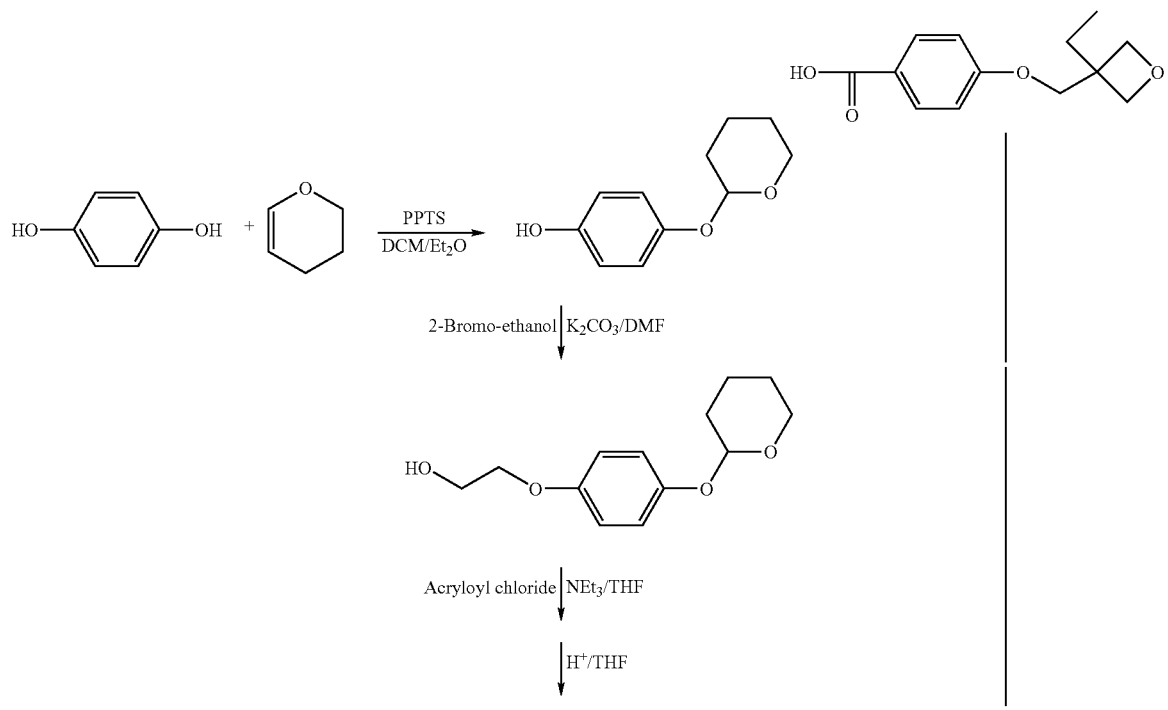

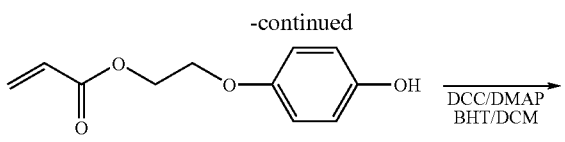
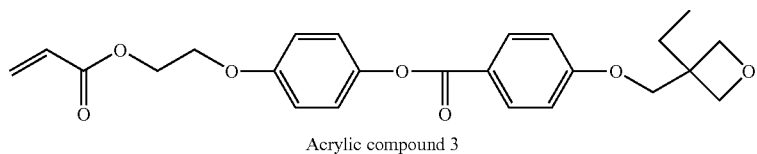
Acrylic compound 3
Reference Example 4
Synthesis of Acrylic Compound 4
In accordance with Scheme 4 below, an acrylic compound 4 was synthesized.
[Scheme 4]
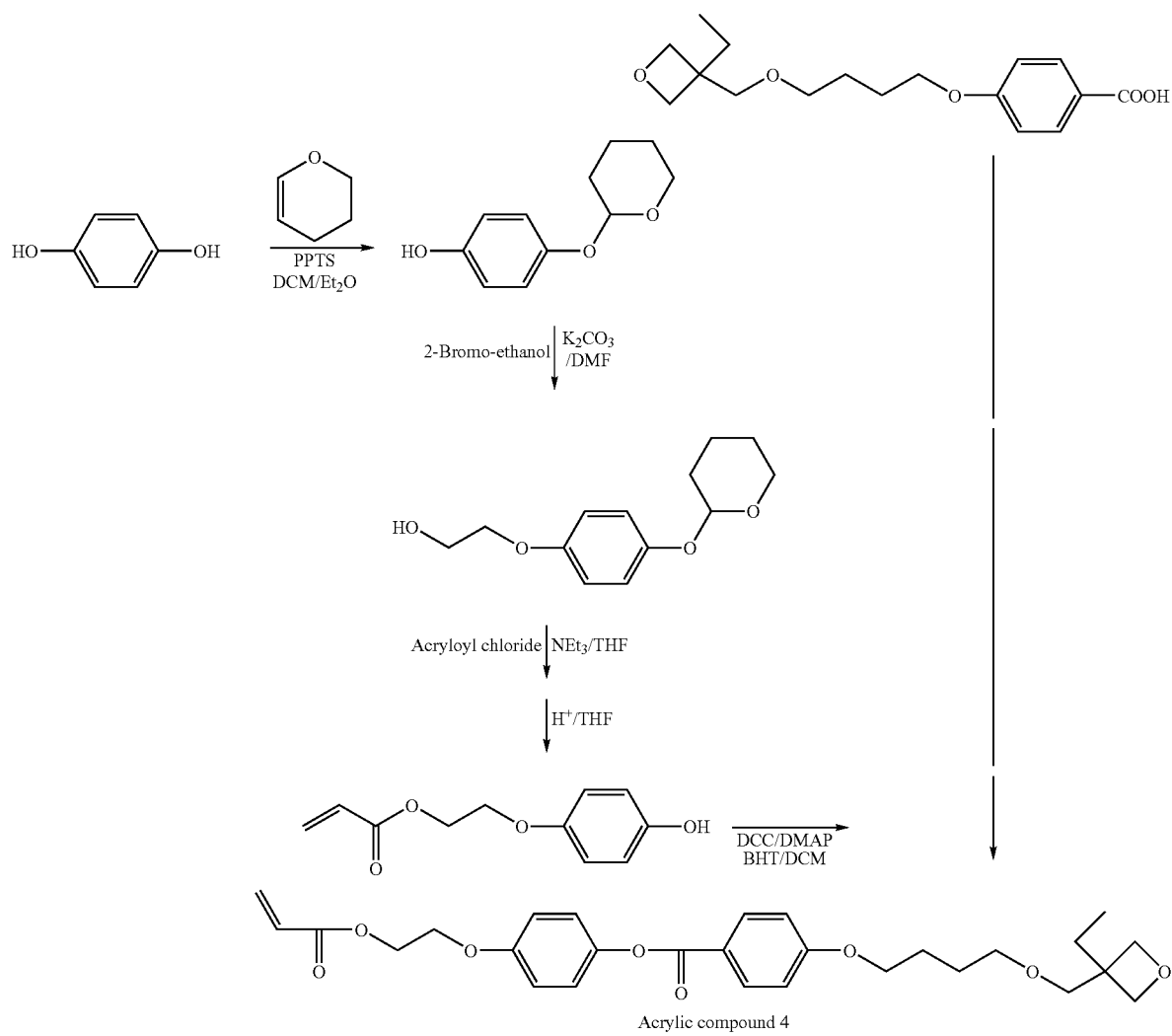
Acrylic compound 4

Reference Example 5

Synthesis of Acrylic Compound 5

In accordance with Scheme 5 below, an acrylic compound 5 was synthesized.

[Scheme 5]

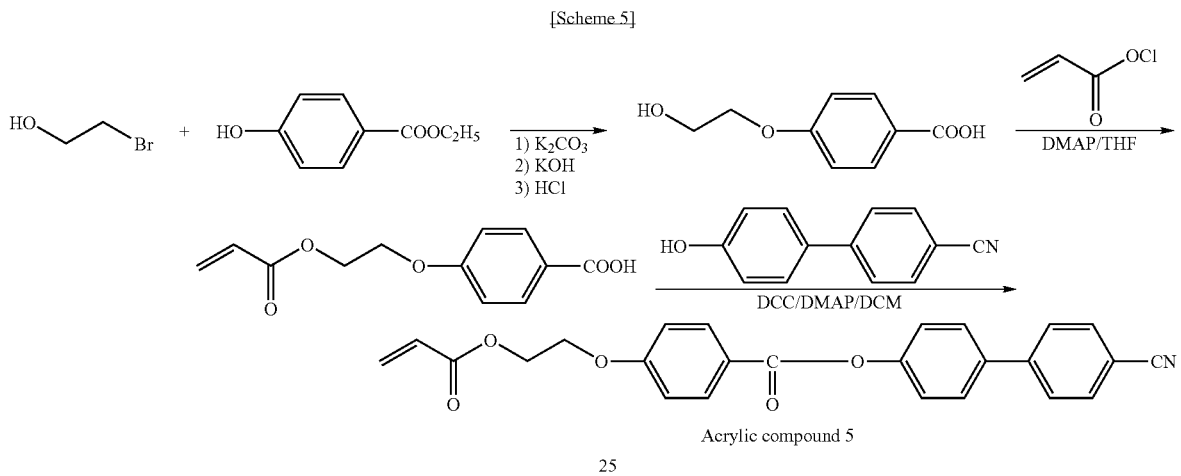

Acrylic compound 5

Reference Example 6

Synthesis of Acrylic Compound 6

In accordance with Scheme 6 below, an acrylic compound 6 was synthesized.

[Scheme 6]

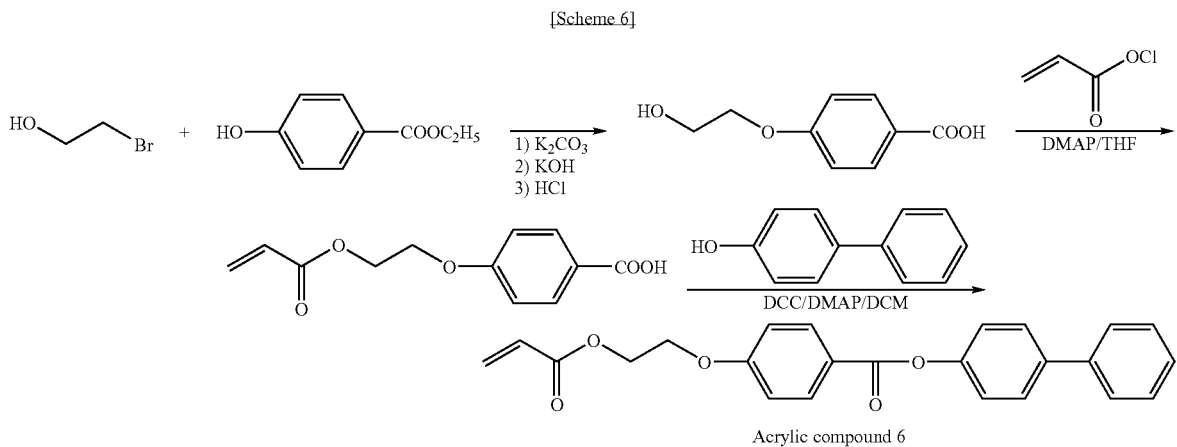

Acrylic compound 6

Reference Example 7

Synthesis of Acrylic Compound 7 Having a Chiral Source

In accordance with Scheme 7 below, an acrylic compound 7 having a chiral source was synthesized.

[Scheme 7]

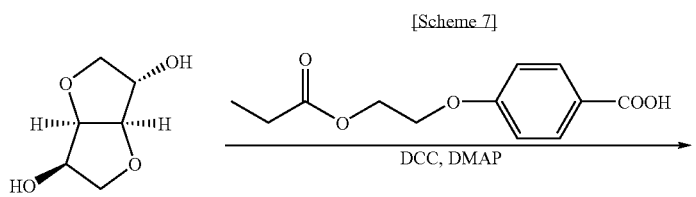

-continued

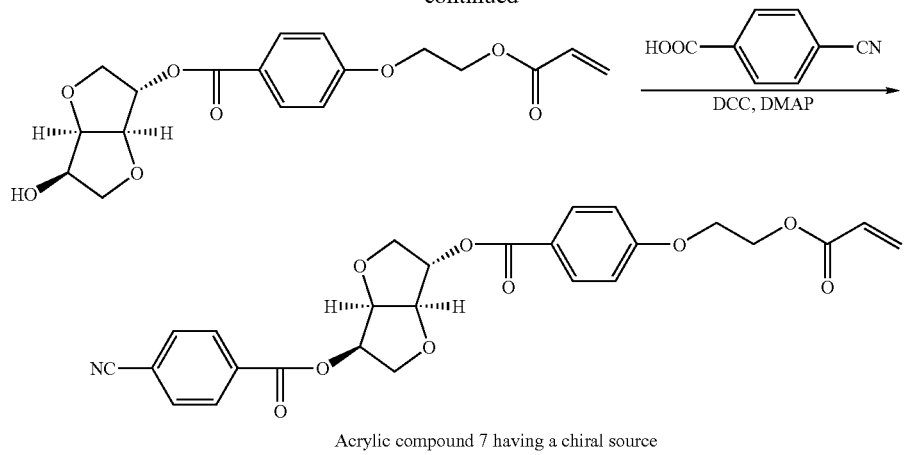

Acrylic compound 7 having a chiral source

Reference Example 8

Synthesis of Side Chain Type Liquid Crystalline Polyacrylate 8

A side chain type liquid crystalline polyacrylate 8 was synthesized by radical-polymerizing 2 parts (molar ratio) of the acrylic compound 3 and 8 parts (molar ratio) of the acrylic compound 5 at a temperature of 90° C. under a nitrogen atmosphere for 6 hours using 2,2'-azobisisobutyronitrile as an initiator and DMF as a solvent and reprecipitating the polymerized product with methanol.

GPC measurement revealed that the weight-average molecular weight of the side chain liquid crystalline polyacrylate 8 was 9,100.

DSC measurement revealed that the glass transition temperature (Tg) was 82° C. It was confirmed from the polarizing microscope observation on the hot stage that the polyacrylate exhibited a nematic liquid crystal phase at the glass transition temperature or higher and the Nm-Iso transition temperature was 248° C.

Reference Example 9

Synthesis of Side Chain Type Liquid Crystalline Polyacrylate 9

A side chain type liquid crystalline polyacrylate 9 was synthesized by radical-polymerizing 2 parts (molar ratio) of the acrylic compound 4, 6 parts (molar ratio) of the acrylic compound 5 and 2 parts (molar ratio) of the acrylic compound 6 at a temperature of 90° C. under a nitrogen atmosphere for 6 hours using 2,2'-azobisisobutyronitrile as an initiator and DMF as a solvent and reprecipitating the polymerized product with methanol.

GPC measurement revealed that the weight-average molecular weight of the side chain liquid crystalline polyacrylate 9 was 9,700.

DSC measurement revealed that the glass transition temperature (Tg) was 78° C. It was confirmed from the polarizing microscope observation on the hot stage that the polyacrylate exhibited a nematic liquid crystal phase at the glass transition temperature or higher and the Nm-Iso transition temperature was 229° C.

Reference Example 10

Synthesis of Side Chain Type Liquid Crystalline Polyacrylate 10

A side chain type liquid crystalline polyacrylate 10 having an oxetanyl group was synthesized by radical-polymerizing 2 parts (molar ratio) of the acrylic compound 3, 7.3 parts (molar ratio) of the acrylic compound 5 and 0.7 part (molar ratio) of the acrylic compound 7 having a chiral source at a temperature of 90° C. under a nitrogen atmosphere for 6 hours using 2,2'-azobisisobutyronitrile as an initiator and DMF as a solvent and reprecipitating the polymerized product with methanol.

GPC measurement revealed that the weight-average molecular weight of the side chain liquid crystalline polyacrylate 10 was 8,900.

DSC measurement revealed that the glass transition temperature (Tg) was 85° C. It was confirmed from the polarizing microscope observation on the hot stage that the polyacrylate exhibited a cholesteric liquid crystal phase at the glass transition temperature or higher and the Ch-Iso transition temperature was 218° C.

Example 1

Synthesis of Dioxetane Compound 1

[Scheme 8]

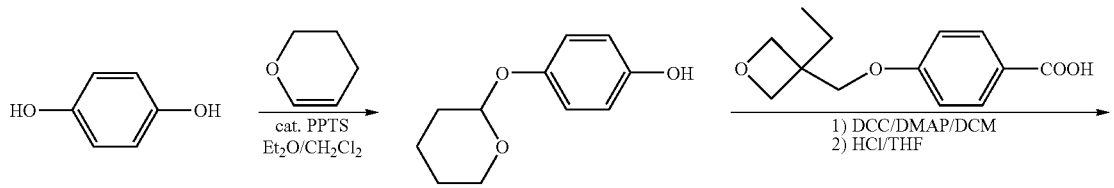

-continued

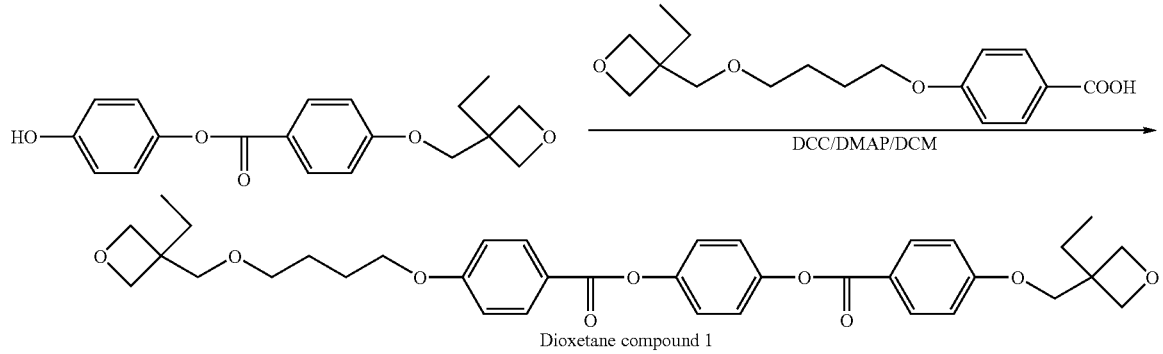
Dioxetane compound 1

In accordance with Scheme 8 above, a dioxetane compound 1 was synthesized using hydroquinone, 3,4-dihydro-2H-pyrane, the intermediate compound 1 having an oxetanyl group and the intermediate compound 2 having an oxetanyl group. The resulting compound was refined by recrystallization with a hexane/ethyl acetate solvent. The recrystallized product was white solid at room temperature.

Figure 2:
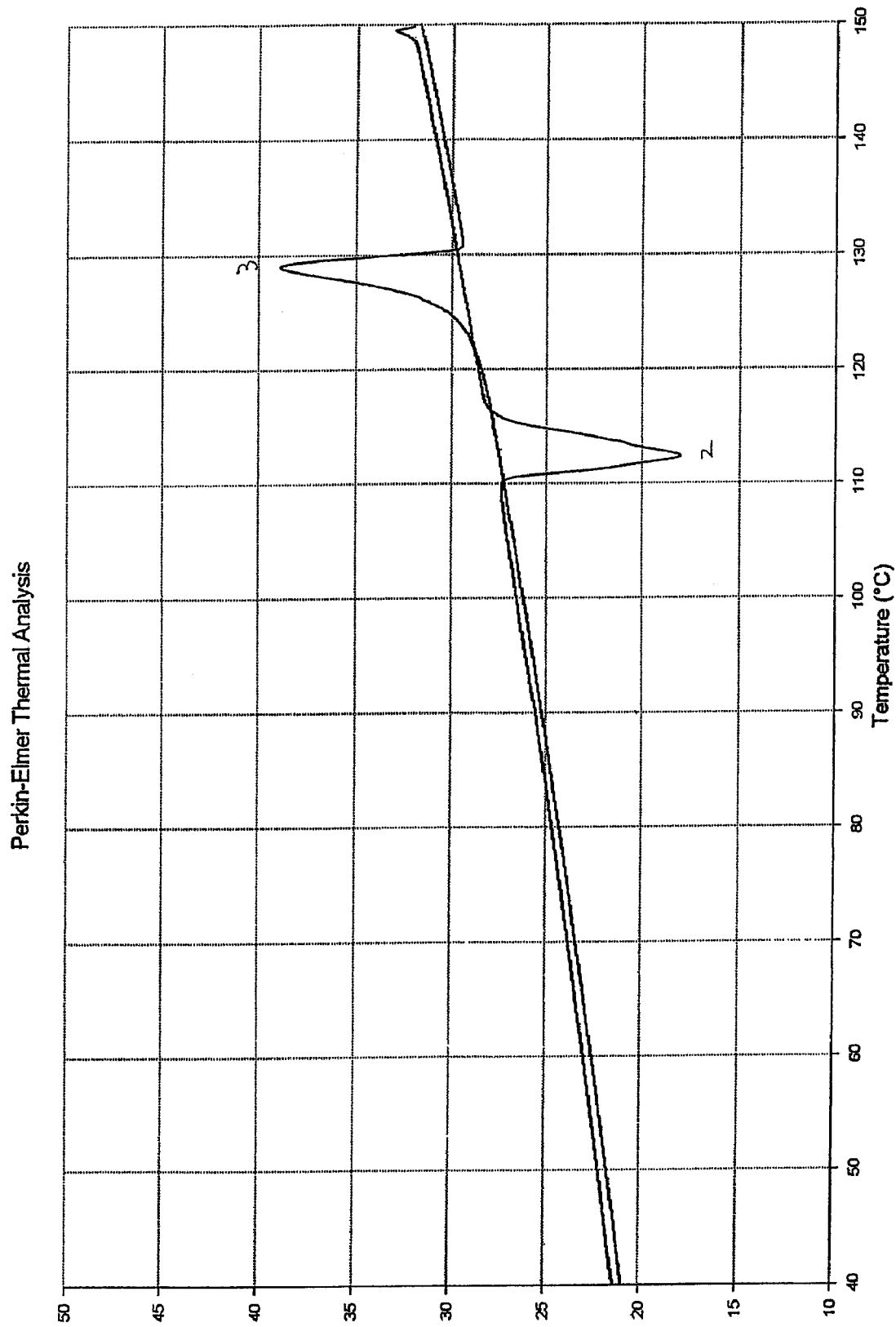
FIG. 2 is the DSC chart of dioxetane compound 1 synthesized in Example 1 wherein the numerals (2, 3) indicate the number of step.

The $^1$H-NMR spectrum of the dioxetane compound 1 is shown in FIG. 1 and the result of the DSC measurement is shown in FIG. 2.

It was confirmed from the result of DSC and polarizing microscope observation that the dioxetane compound 1 exhibited C-Iso phase behavior and no liquid crystallinity.

(1) Peak positions of dioxetane compound 1 in $^1$H-NMR (CDCl$_3$; TMS)

δ 0.9(t, 3H), 1.0(t, 3H), 1.7(dd, 2H), 1.8(m, 2H), 1.9(m, 4H), 3.6(t, 4H), 4.1(t, 2H), 4.2(s, 2H), 4.4(d, 2H), 4.5(d, 2H), 4.5(d, 2H), 4.6(d, 2H), 7.0(dd, 4H), 7.3(s, 2H), 8.2(dd, 4H)

(2) Peak positions of dioxetane compound 1 in $^{13}$C-NMR (CDCl$_3$; TMS)

δ 8.46, 26.30, 26.39, 26.89, 27.02, 43.37, 43.63, 68.24, 70.69, 71.26, 73.72, 78.20, 78.73, 114.52, 114.60, 121.68, 121.22, 122.84, 122.88, 132.52, 132.57, 148.57, 148.65, 163.56, 163.69, 164.92, 165.00

Example 2

Synthesis of Dioxetane Compound 2

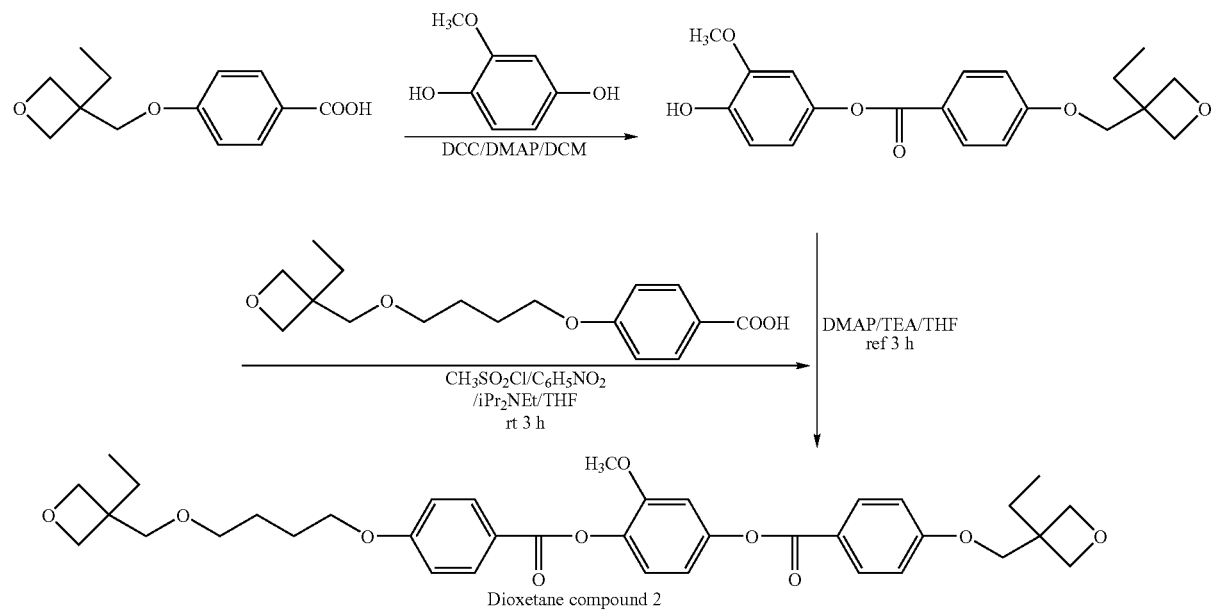
Dioxetane compound 2

In accordance with Scheme 9 above, a dioxetane compound 2 was synthesized. The resulting compound was refined in a hexane/ethyl acetate solvent with a silica gel chromatography. The refined product was white solid at room temperature.

Figure 3:
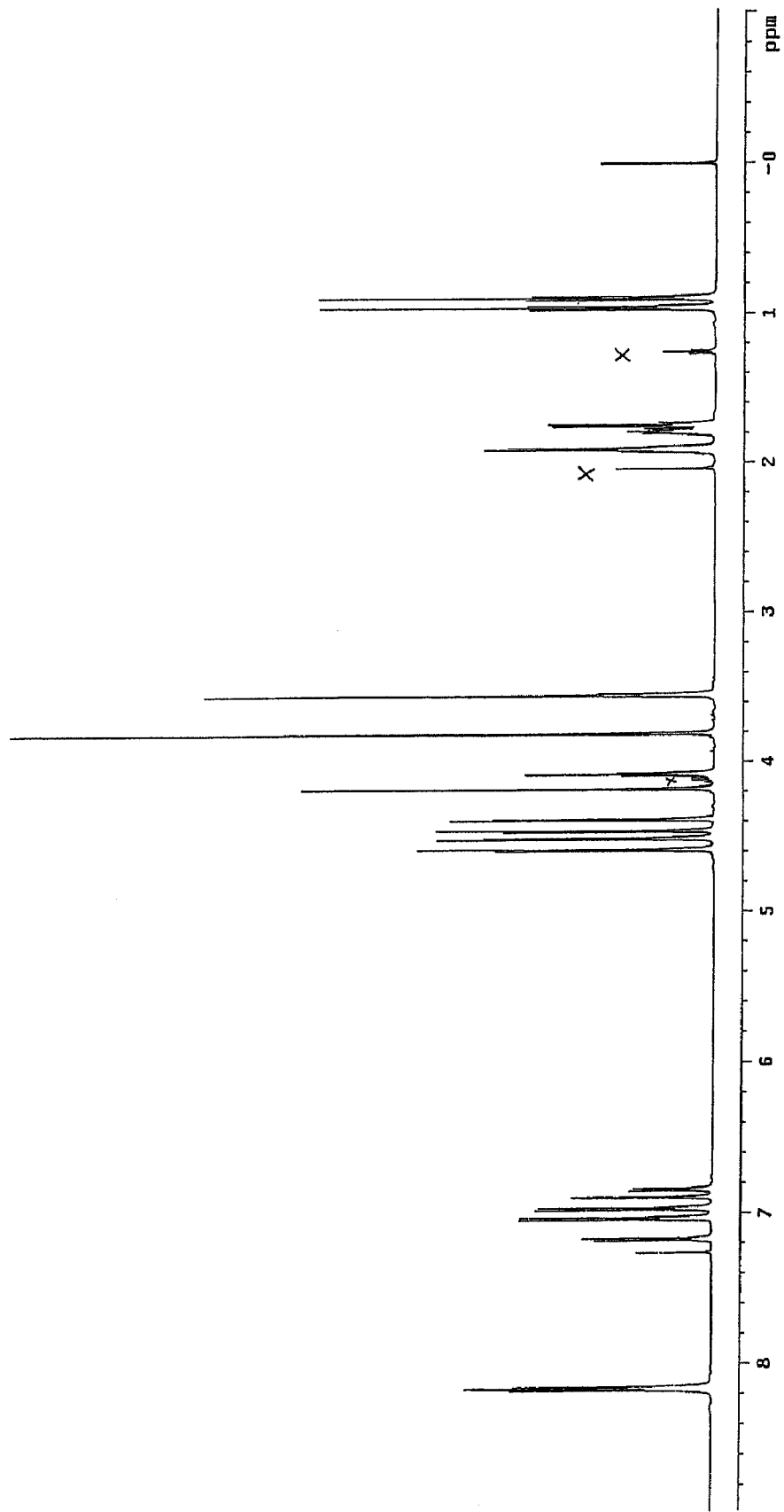
FIG. 3 is the $^1$NMR spectrum of dioxetane compound 2 synthesized in Example 2, wherein the mark "x" indicates the peak of the solvent.
Figure 4:
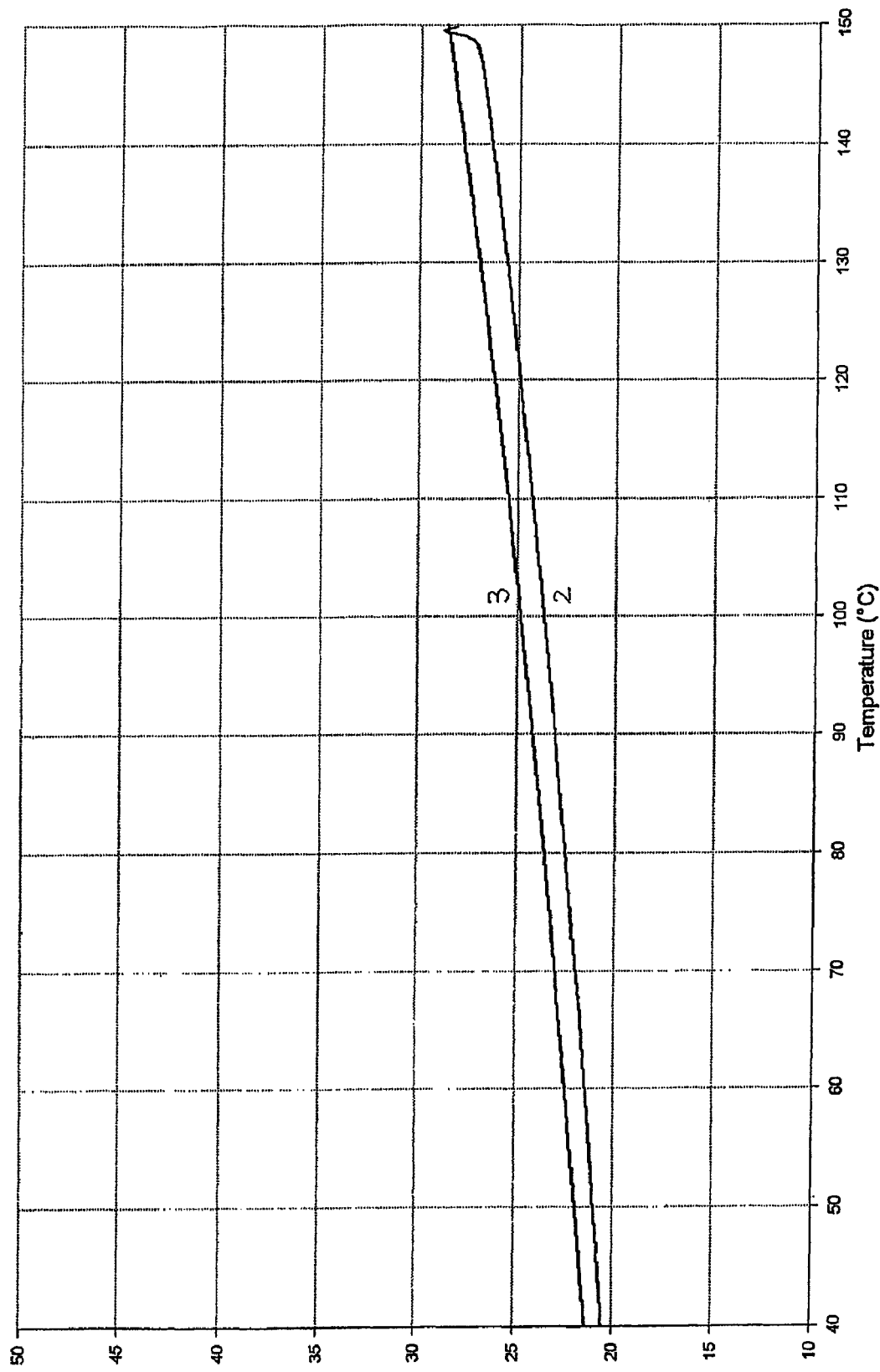
FIG. 4 is the DSC chart of dioxetane compound 2 synthesized in Example 2 wherein the numerals (2, 3) indicate the number of step.

The $^1$H-NMR spectrum of the dioxetane compound 2 is shown in FIG. 3 and the result of the DSC measurement is shown in FIG. 4.

In Steps 2 and 3 of DSC, no endothermic peak was observed. The presence of C-Iso phase behavior was confirmed through the polarizing microscope observation on the hot stage only when the temperature was increased. It was confirmed from these results that the dioxetane compound 2 had no liquid crystal phase.

(1) Peak positions of dioxetane compound 2 in $^1$H-NMR (CDCl$_3$; TMS)

δ 0.9(t, 3H), 1.0(t, 3H), 1.8(m, 4H), 1.9(m, 4H), 3.6(m, 4H), 3.8(s, 3H), 4.1(m, 2H), 4.2(s, 2H), 4.4(d, 2H), 4.5(d, 2H), 4.5(d, 2H), 4.6 (d, 2H), 6.9(m, 1H), 6.9(d, 1H), 7.0(d, 2H), 7.1(d, 2H), 7.2(s, 1H), 8.2(m, 4H)

(2) Peak positions of dioxetane compound 2 in $^{13}$C-NMR (CDCl$_3$; TMS)

δ 8.26, 26.10, 26.20, 26.69, 26.81, 43.19, 43.44, 56.12, 68.00, 70.50, 71.06, 73.54, 78.03, 78.56, 106.84, 113.55, 114.24, 114.39, 121.45, 122.05, 123.21, 132.37, 132.45, 137.66, 149.28, 151.96, 163.36, 164.44, 164.71

Example 3

Synthesis of Dioxetane Compound 3

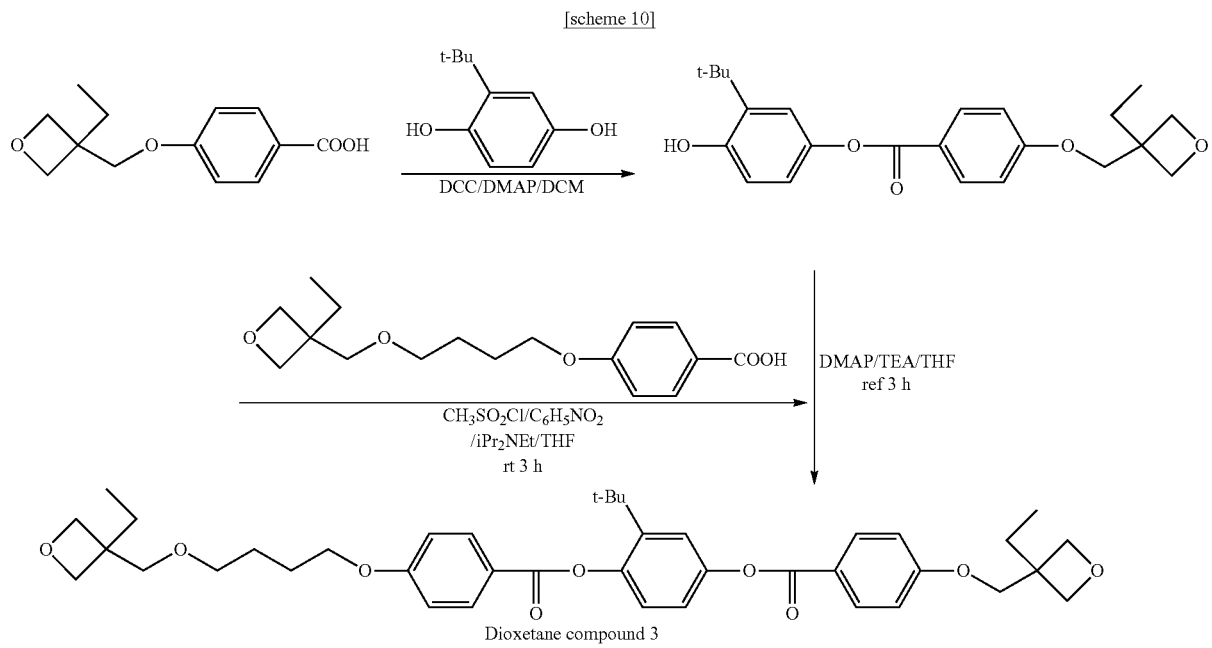

[scheme 10]

In accordance with Scheme 10 above, a dioxetane compound 3 was synthesized. The resulting compound was refined in a hexane/ethyl acetate solvent with a silica gel chromatography.

Figure 5:
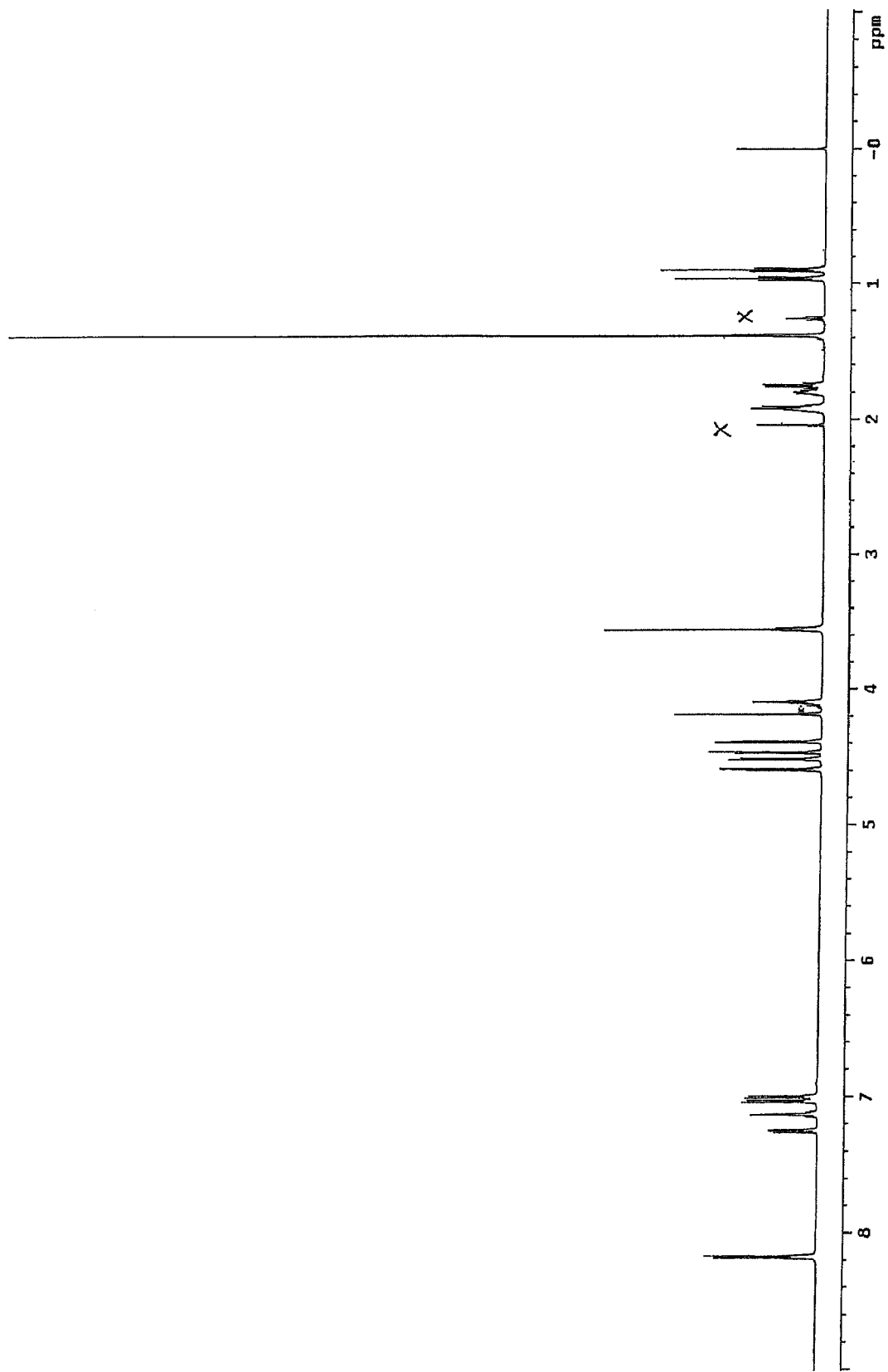
FIG. 5 is the $^1$NMR spectrum of dioxetane compound 3 synthesized in Example 3, wherein the mark "x" indicates the peak of the solvent.
Figure 6:
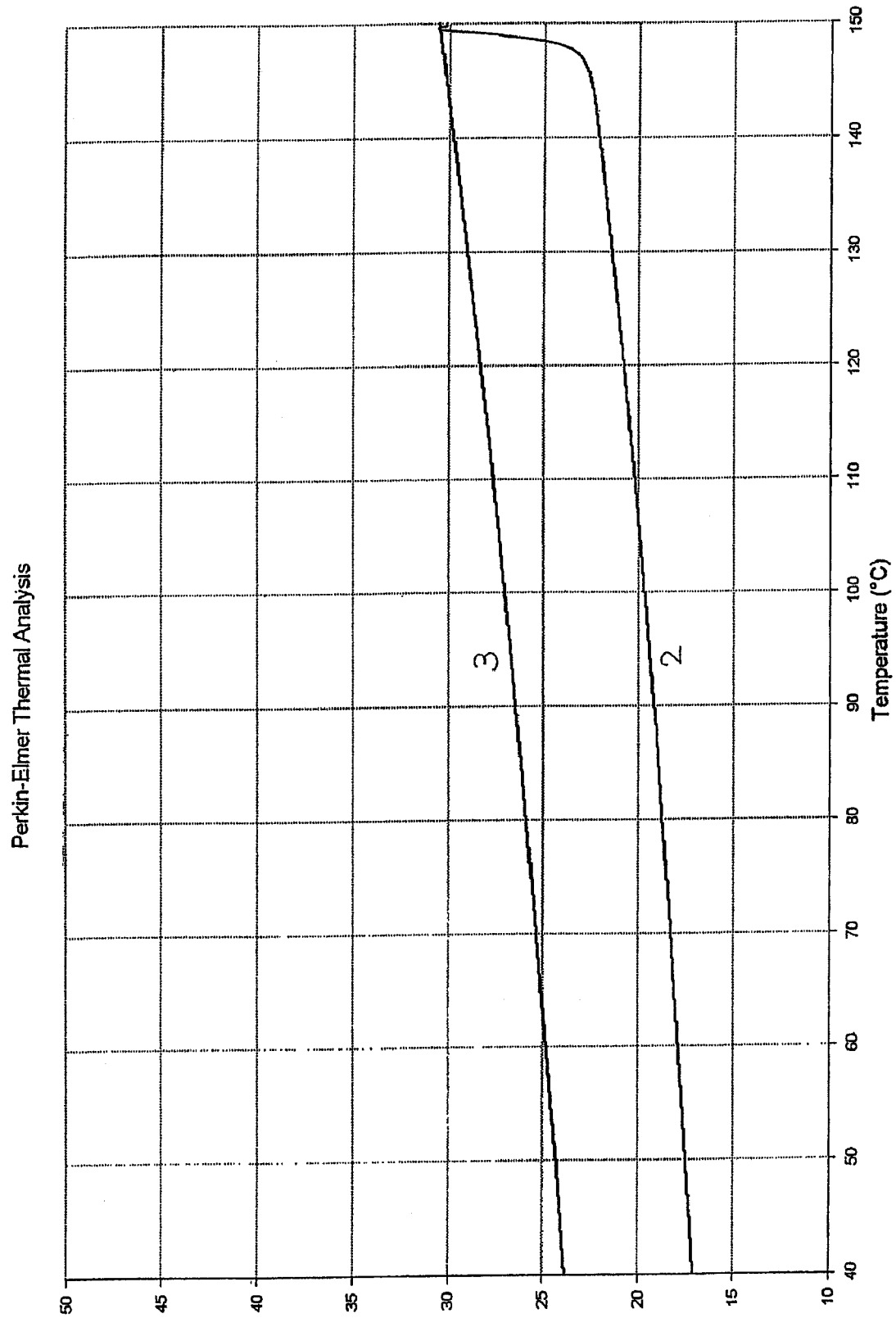
FIG. 6 is the DSC chart of dioxetane compound 3 synthesized in Example 3 wherein the numerals (2, 3) indicate the number of step.

The $^1$H-NMR spectrum of the dioxetane compound 3 is shown in FIG. 5 and the result of the DSC measurement is shown in FIG. 6.

In Steps 2 and 3 of DSC, no endothermic peak was observed. The presence of C-Iso phase behavior was confirmed through the polarizing microscope observation on the hot stage only when the temperature was increased. It was confirmed from these results that the dioxetane compound 3 had no liquid crystal phase.

(1) Peak positions of dioxetane compound 3 in $^1$H-NMR (CDCl$_3$; TMS)

δ 0.9(t, 3H), 1.0(t, 3H), 1.4(s, 9H), 1.8 (m, 4H), 1.9(m, 4H), 3.6(s, 4H), 4.1(m, 2H), 4.2(s, 2H), 4.4(d, 2H), 4.5(d, 2H), 4.5(d, 2H), 4.6(d, 2H), 7.0(dd, 4H), 7.1((m, 2H), 7.2(dd, 1H), 8.2(d, 4H)

(2) Peak positions of dioxetane compound 3 in $^{13}$C-NMR (CDCl$_3$; TMS)

δ 8.25, 26.09, 26.20, 26.70, 26.81, 30.12, 34.72, 43.18, 43.43, 68.04, 70.48, 71.04, 73.53, 78.04, 78.55, 114.35, 114.44, 120.01, 120.56, 121.81, 122.22, 125.06, 132.35, 132.39, 142.89, 146.84, 148.14, 163.29, 163.50, 164.88, 165.06

Comparative Example 1

Synthesis of Liquid Crystalline Dioxetane Compound 4

In accordance with Scheme 11 below, a liquid crystalline dioxetane compound 4 was synthesized.

[Scheme 11]

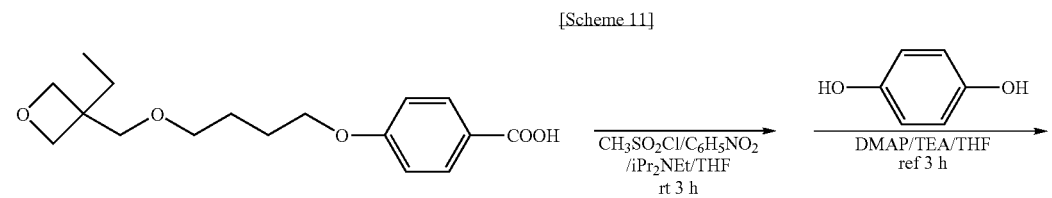

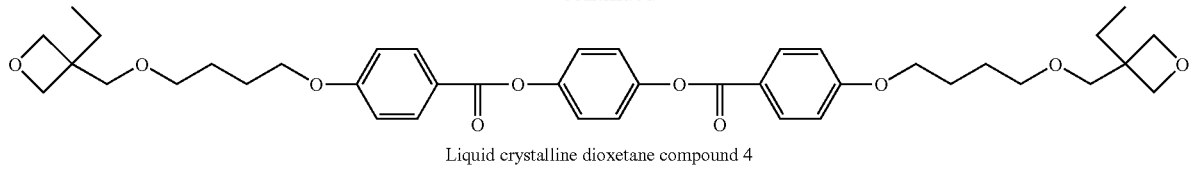

Liquid crystalline dioxetane compound 4

Figure 7:
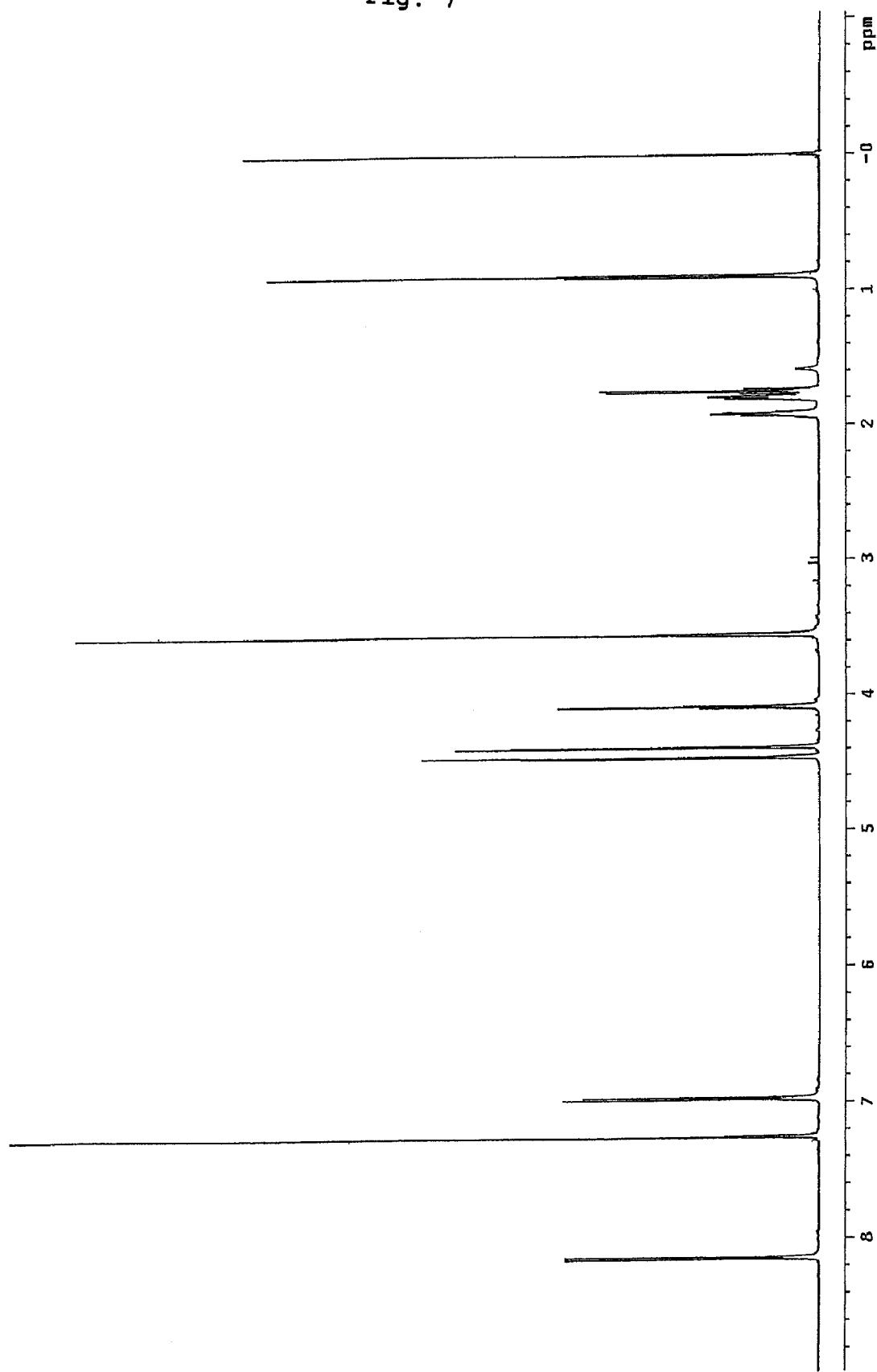
FIG. 7 is the $^1$NMR spectrum of dioxetane compound 4 synthesized in Comparative Example 1.
Figure 8:
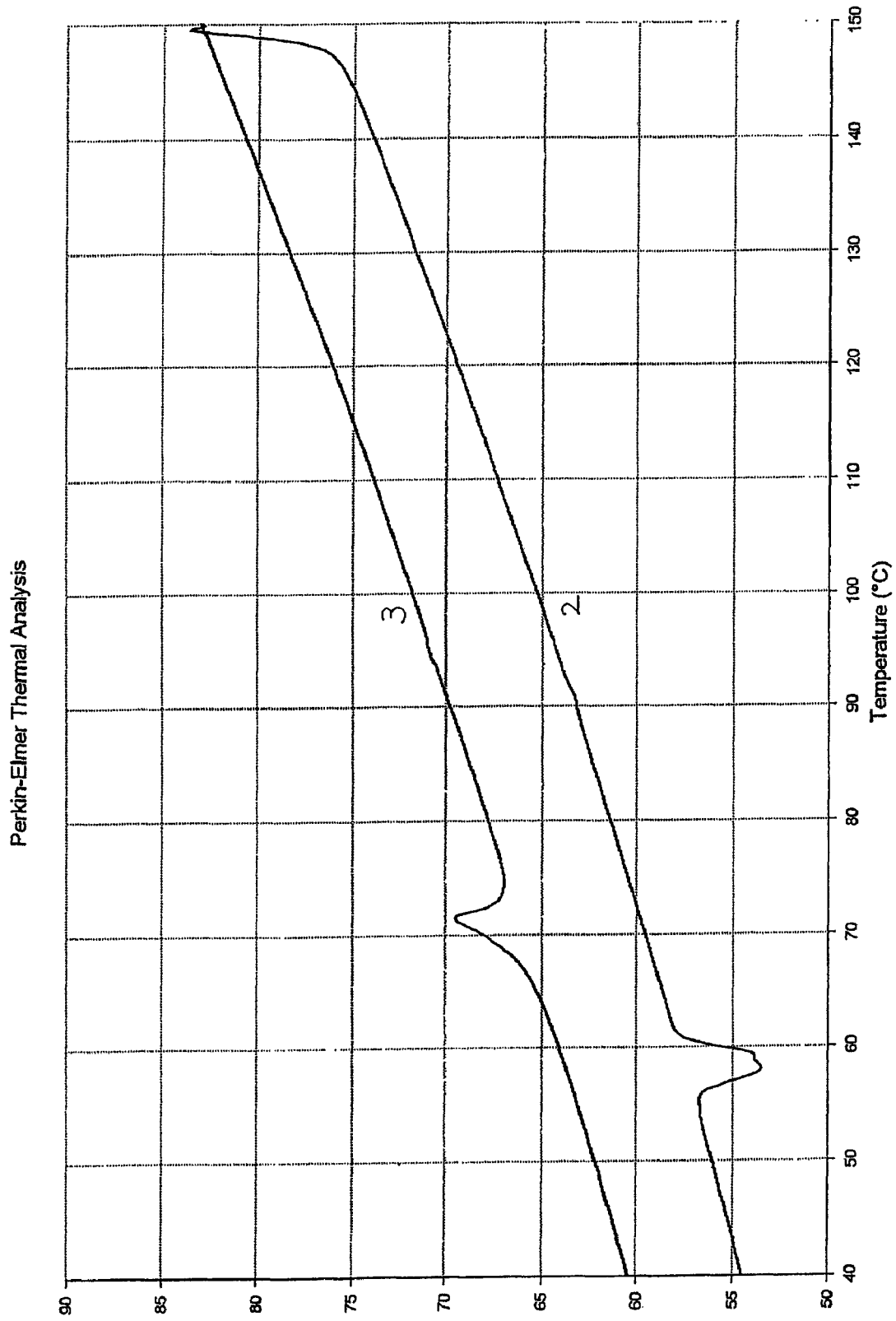
FIG. 8 is the DSC chart of dioxetane compound 4 synthesized in Comparative Example 1 wherein the numerals (2, 3) indicate the number of step.

The $^1$H-NMR spectrum of the dioxetane compound 4 is shown in FIG. 7 and the result of the DSC measurement is shown in FIG. 8.

In Step 3 of DSC, the endothermic peaks of C-Nm and Nm-Iso were observed at 72° C. and 95° C., respectively. Through the polarizing microscope observation on the hot plate, C-Nm and Nm-Iso phase behaviors were observed at temperatures in the vicinity that are the substantially same as those at each peak observed through DSC. It was confirmed from these results that the dioxetane compound 4 had a liquid crystal phase.

Example 4

Production of Optical Film Using Side Chain Type Liquid Crystalline Polyacrylate 8

In 9 ml of cyclohexanone were dissolved 0.8 g of the side chain type liquid crystalline polyacrylate 8 synthesized in Reference Example 8 and 0.2 g of the dioxetane compound 1 produced in Example 1, followed by addition of 0.30 g of a propylene carbonate solution of 50 percent of triarylsulfonium hexafluoroantimonate (a reagent manufactured by Aldrich Co.) at a dark place and filtration of insolubles with a polytetrafluoroethylene filter with a pore size of 0.45 µm thereby producing a solution of a cationically polymerizable composition.

The solution was spin-coated over a 100 µm thickness polyimide film "KAPTON" manufactured by DU PONT-TORAY CO., LTD., whose surface had been subjected to a rubbing treatment with a rayon cloth, and then dried on a hot plate kept at 60° C. While the resulting cationically polymerizable composition layer on the polyimide film was heated at a temperature of 145° C., the layer was irradiated with an ultraviolet light of an integrated irradiation dose of 300 mJ/cm$^2$ from a high-pressure mercury lamp under an air atmosphere and then cooled thereby producing a cured cationically polymerizable composition layer.

Since the polyimide film used as a substrate was brown and thus not preferable as an optical film, the resulting cured cationically polymerizable composition layer was transferred via an ultraviolet curing type adhesive "UV-3400" (manufactured by Toagosei Co., Ltd.) onto a triacetyl cellulose (TAC) film thereby producing an optical film with retardation. More specifically, the UV-3400 with a thickness of 5 µm was coated over the cured cationically polymerizable composition layer on the polyimide film and laminated with a TAC film. After the laminate was subjected to an irradiation of ultraviolet light of 400 mJ/cm$^2$ from the TAC film side so as to cure the adhesive, the polyimide film was released.

As a result of observation of the resulting optical film through a polarizing microscope, it was confirmed that the film exhibited a monodomain uniform nematic hybrid liquid crystal orientation having no disclination and the Δnd viewed from the front was 102 nm. The Δnd viewed from a position tilted at an angle of 40 degrees from the vertical direction along the rubbing axis was 142 nm while the Δnd viewed from an opposite position tilted at an angle of −40 degrees was 46 nm. The both Δnds were asymmetrical. From these observations, it was recognized that the film was aligned in a nematic hybrid orientation structure because there was no point wherein the Δnd is zero nm at any angle. The thickness of the liquid crystalline composition layer of the resulting liquid crystal film was 0.85 µm.

Further, only a cationically polymerizable composition portion was scrapped off from the optical film and measured for glass transition temperature (Tg) using the DSC. As a result, no Tg was observed. A cationically polymerizable composition portion was again scrapped off from the optical film and measured for IR. As a result, no peak peculiar to unreacted oxetane group that is usually seen in the vicinity of 980 cm$^{-1}$ was observed.

The optical film was attached via a non-carrier tacky adhesive onto a 2 mm thickness sodalime glass plate. Over the film was attached a polarizer (SQW-862 manufactured by Sumitomo Chemical Co., Ltd.) such that the rubbing direction of the polyimide film was aligned with the absorption axis of the polarizer. This sample was observed through the polarizer on a backlight and found to be a uniform film. After the sample was kept in a thermostat whose temperature was set at 110° C., for 100 hours, it was taken out therefrom and similarly observed. As a result, any particular change or disorder in the liquid crystal orientation was not observed.

The pencil hardness of the cationically polymerizable composition layer surface of the film was on the order of 4H and thus it was confirmed that the film had a sufficient hardness. As described above, it was found that the use of the side chain type liquid crystalline polyacrylate 8 rendered it possible to produce an optical film which was aligned excellently in a liquid crystal orientation state and improved in thermal stability and strength after being fixed in the liquid crystal orientation.

Comparative Example 2

In 9 ml of cyclohexanone were dissolved 0.8 g of the side chain type liquid crystalline polyacrylate 8 synthesized in Reference Example 8 and 0.2 g of the liquid crystalline dioxetane compound 4 produced in Comparative Example 1, followed by addition of 0.30 g of a propylene carbonate solution of 50 percent of triarylsulfonium hexafluoroantimonate (a reagent manufactured by Aldrich Co.) at a dark place and filtration of insolubles with a polytetrafluoroethylene filter with a pore size of 0.45 µm thereby producing a solution of a cationically polymerizable composition.

The solution was spin-coated over a 100 µm thickness polyimide film "KAPTON" manufactured by DU PONT-TORAY CO., LTD., whose surface had been subjected to a rubbing treatment with a rayon cloth, and then dried on a hot plate kept at 60° C. While the resulting cationically polymerizable composition layer on the polyimide film was heated at a temperature of 145° C., the layer was irradiated with an ultraviolet light of an integrated irradiation dose of 300 mJ/cm$^2$ from a high-pressure mercury lamp under an air atmosphere and then cooled thereby producing a cured cationically polymerizable composition layer.

Since the polyimide film used as a substrate was brown and thus not preferable as an optical film, the resulting cured cationically polymerizable composition layer was transferred via an ultraviolet curing type adhesive "UV-3400" (manufactured by Toagosei Co., Ltd.) onto a triacetyl cellulose (TAC) film thereby producing an optical film with retardation. More specifically, the UV-3400 with a thickness of 5 μm was coated over the cured cationically polymerizable composition layer on the polyimide film and laminated with a TAC film. After the laminate was subjected to an irradiation of ultraviolet light of 400 mJ/cm$^2$ from the TAC film side so as to cure the adhesive, the polyimide film was released.

As a result of observation of the resulting retardation film through a polarizing microscope, sea-island patterns were observed from which phase separation assumedly occurred.

Comparative Example 3

Phase separation seemed to occur in the compositional structure of Comparative Example 2. A retardation film was produced with the same procedures of Comparative Example 2 except that the amount of a propylene carbonate solution of 50 percent of triarylsulfonium hexafluoroantimonate (a reagent manufactured by Aldrich Co.) was changed to 0.05 g.

When a propylene carbonate solution of 50 percent of triarylsulfonium hexafluoroantimonate (a reagent manufactured by Aldrich Co.) is not added in the composition of Comparative Example 2, no cure occurs even though a light is irradiated from a high-pressure mercury lamp but sea-island patterns regarded as phase separation does not emerge.

As a result of observation of the resulting retardation film through a polarizing microscope, it was confirmed that the retardation film exhibited a monodomain uniform nematic hybrid liquid crystal orientation having no disclination and the And viewed from the front was 85 nm.

Further, only a cationically polymerizable composition portion was scrapped off from the retardation film and measured for glass transition temperature (Tg) using the DSC. As a result, no Tg was observed. However, a cationically polymerizable composition portion was scrapped off from the retardation film and the IR of the scraped portion was measured. As a result, a peak peculiar to unreacted oxetane group that is usually seen in the vicinity of 980 cm$^{-1}$ was observed. It was confirmed that unreacted group existed.

The retardation film was attached via a non-carrier tacky adhesive onto a 2 mm thickness sodalime glass plate. Over the film was attached a polarizer (SQW-862 manufactured by Sumitomo Chemical Co., Ltd.) such that the rubbing direction of the polyimide film was aligned with the absorption axis of the polarizer. This sample was observed through the polarizer on a backlight and found to be a uniform film. After the sample was kept in a thermostat whose temperature was set at 110° C., for 100 hours, it was taken out therefrom and similarly observed. As a result, disorder in the liquid crystal orientation was partially observed.

The pencil hardness of the cationically polymerizable composition layer surface of the film was on the order of 2H.

Example 5

Production of Optical Film 1 Using Side Chain Type Liquid Crystalline Polyacrylate 9

In 15.00 g of cyclohexanone were dissolved 5.00 g of the side chain type liquid crystalline polyacrylate 9 synthesized in Reference Example 9 and 1.00 g of the dioxetane compound 2, followed by addition of 0.12 g of "UVI-6992" manufactured by DOW Chemical Company (a 50 percent propylene carbonate solution) and filtration of insolubles with a polytetrafluoroethylene filter with a pore size of 0.45 μm thereby producing a solution of a cationically polymerizable composition.

The resulting solution was spin-coated over a 50 μm thickness polyethylene naphthalate film "Teonex Q-51" (manufactured by Teijin Dupont Films Japan Ltd.) whose surface had been subjected to a rubbing treatment with a rayon cloth and then a hot air of about 60° C. was slowly blown to the film to remove the solvent. Thereafter, the film was heated at a temperature of 150° C. in an oven for 3 minutes so as to form a uniform liquid crystal orientation (film 1a). The pencil hardness of the film 1a was 6B or less which was weak.

The film 1a was irradiated with an ultraviolet light of an integrated irradiation dose of 450 mJ/cm$^2$ from a high-pressure mercury lamp thereby producing a cured cationically polymerizable composition layer (film 1b). Since the polyethylene naphthalate film used as a substrate had birefringence and thus is not preferable, the film 1b was transferred via an ultraviolet curing type adhesive "UV-3400" (manufactured by Toagosei Co., Ltd.) onto a TAC film thereby obtaining an optical film 1. The UV-3400 with a thickness of 5 μm was coated over the cured cationically polymerizable composition layer on the polyethylene naphthalate film and laminated with a TAC film. After the laminate was subjected to an irradiation of ultraviolet light of 400 mJ/cm$^2$ from the TAC film side so as to cure the adhesive, the polyethylene naphthalate film was released.

As a result of observation of the resulting optical film 1 through a polarizing microscope, it was confirmed that the film exhibited a monodomain uniform nematic hybrid liquid crystal orientation having no disclination and the Δnd viewed from the front was 120 nm. The average tilt angle was 28 degrees and the thickness of the cationically polymerizable composition layer was 0.83 μm.

Further, only a cationically polymerizable composition portion was scrapped off from the optical film 1 and measured for glass transition temperature (Tg) using the DSC. As a result, no Tg was observed. The pencil hardness of the cationically polymerizable composition layer surface of the optical film 1 was measured and found to be on the order of 2H, and thus it was confirmed that the film had a sufficient hardness.

Example 6

Production of Optical Film 2 Using Side Chain Type Liquid Crystalline Polyacrylate 10

In 10 g of cyclohexanone were dissolved 0.8 g of the side chain type liquid crystalline polyacrylate 10 synthesized in Reference Example 10 and 0.2 g of the dioxetane compound 2, followed by addition of 0.1 g of "UVI-6992" manufactured by DOW Chemical Company (a 50 percent propylene carbonate solution) and filtration of insolubles with a polytetrafluoroethylene filter with a pore size of 0.45 μm thereby producing a solution of a cationically polymerizable composition.

The resulting solution was spin-coated over a 50 μm thickness polyethylene naphthalate film "Teonex Q-51" (manufactured by Teijin Dupont Films Japan Ltd.) whose surface had been subjected to a rubbing treatment with a rayon cloth and then a hot air of about 60° C. was slowly blown to the film to remove the solvent. Thereafter, the film was heated at a temperature of 150° C. in an oven for 3 minutes so as to form a uniform liquid crystal orientation.

The film was irradiated with an ultraviolet light of an integrated irradiation dose of 300 mJ/cm² from a high-pressure mercury lamp thereby producing a cured cationically polymerizable composition layer. Since the polyethylene naphthalate film used as a substrate had birefringence and thus is not preferable, the film was transferred via an ultraviolet curing type adhesive "UV-3400" (manufactured by Toagosei Co., Ltd.) onto a TAC film thereby obtaining an optical film 2. More specifically, the UV-3400 with a thickness of 5 μm was coated over the cured cationically polymerizable composition layer on the polyethylene naphthalate film and laminated with a TAC film. After the laminate was subjected to an irradiation of ultraviolet light of 500 mJ/cm² from the TAC film side so as to cure the adhesive, the polyethylene naphthalate film was released.

As a result of observation of the resulting optical film 2 through a polarizing microscope, it was confirmed that the film exhibited a monodomain cholesteric liquid crystal orientation having no disclination. The film had a selective reflection light peculiar to the cholesteric orientation when viewed from the front. When the transmission spectrum of the optical film 2 was evaluated through a spectroscope, a region wherein the transmitted light peculiar to the selective reflection was decreased was observed around 700 nm. Further, only a cationically polymerizable composition portion was scrapped off from the optical film 2 and measured for glass transition temperature (Tg) using the DSC. As a result, no Tg was observed. The pencil hardness of the cationically polymerizable composition layer surface of the film 2 was measured and found to be on the order of 2H, and thus it was confirmed that the film had a sufficient hardness.

Example 7

Figure 9:
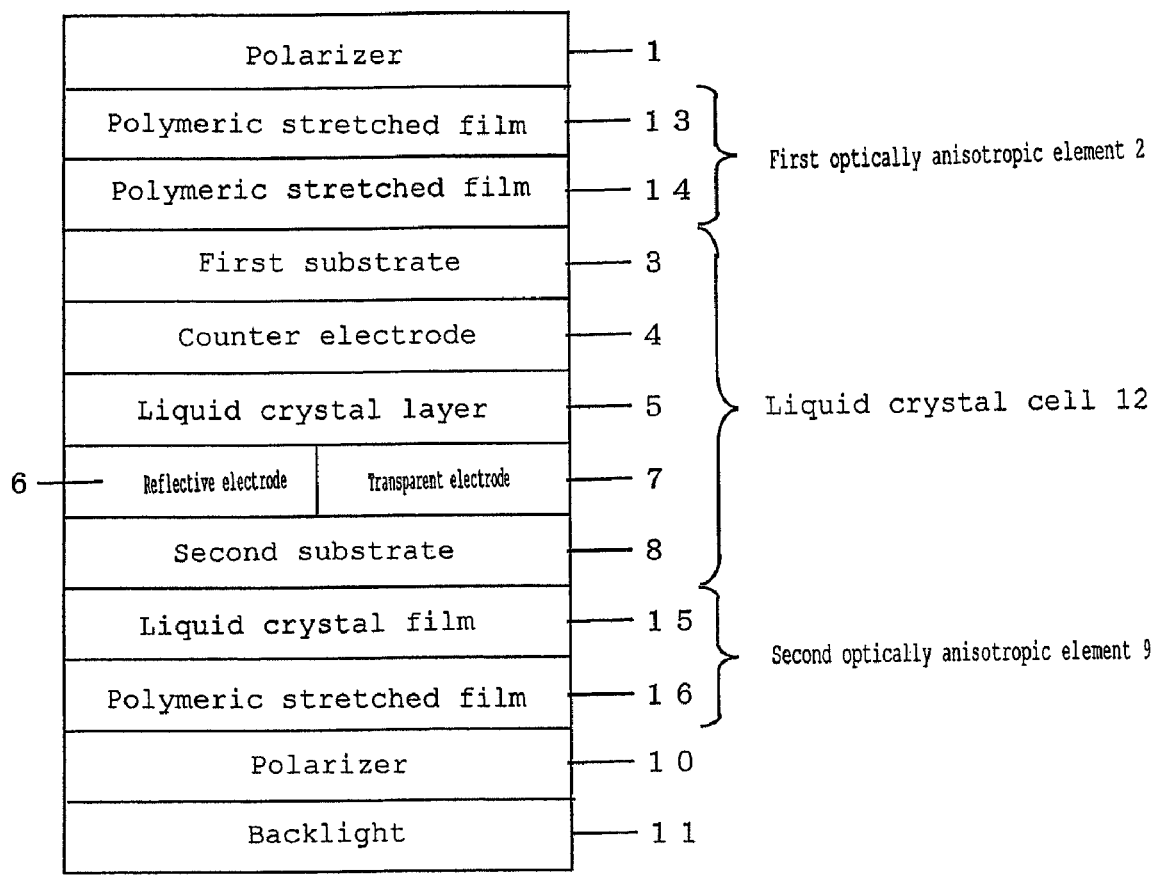
FIG. 9 is a schematic view indicating the layer structure of Example 7.
Figure 10:
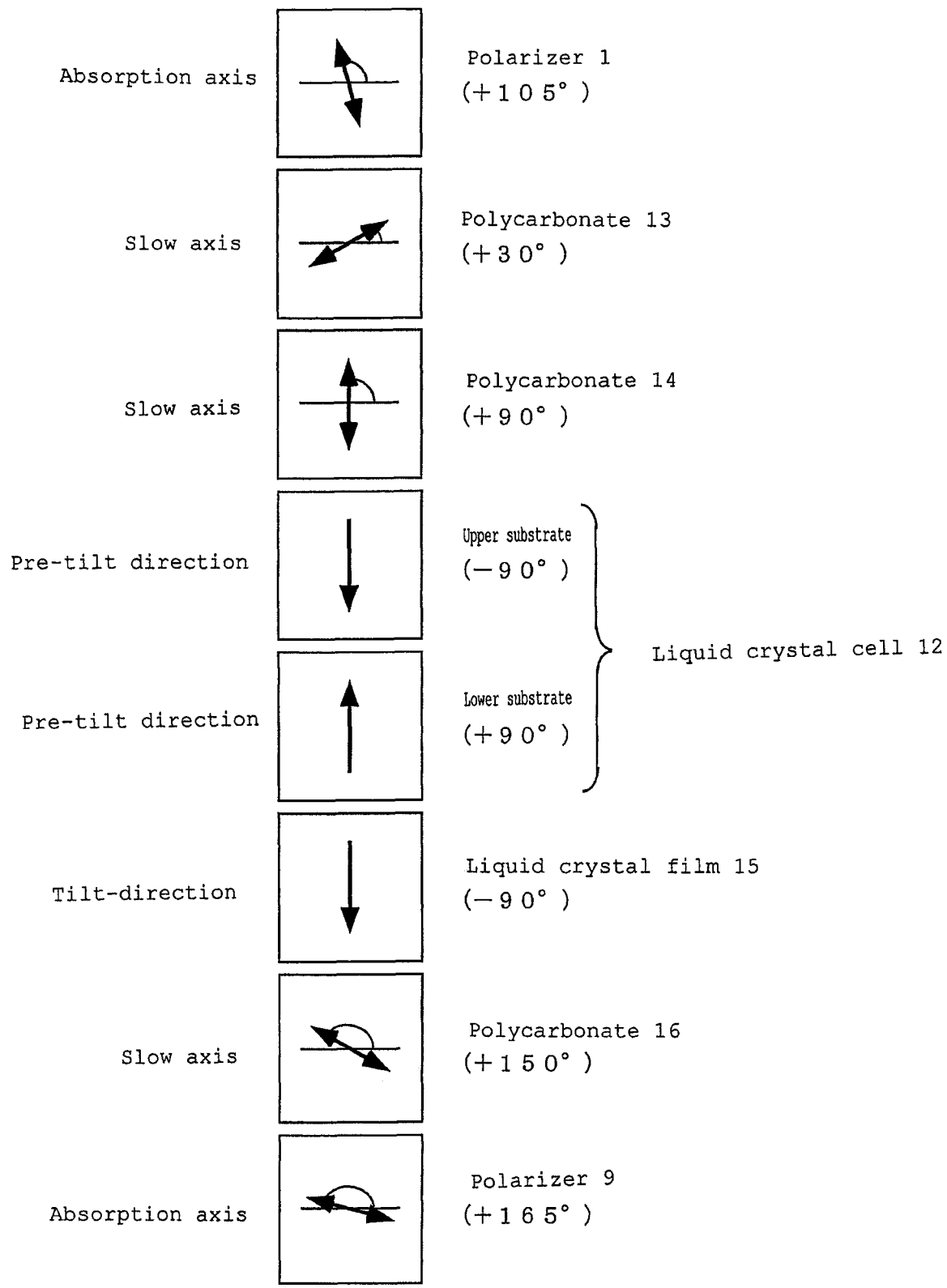
FIG. 10 is a view indicating the axial orientation of each layer of Example 7.

A transflective liquid crystal display device as shown in FIG. 9 was produced. The axial orientation of each layer is shown in FIG. 10. In FIG. 9, on a second substrate 8 are arranged a reflective electrode 6 formed from a highly reflective material such as Al and a transparent electrode 7 formed from a highly transparent material such as ITO while on a first substrate 3 is arranged a counter electrode 4. A liquid crystal layer 5 formed from a liquid crystalline material exhibiting a positive dielectric constant anisotropy is sandwiched between the reflective and transparent electrodes 6, 7 and the counter electrode 4. On the side of the first substrate 3, opposite to the side on which the counter electrode 4 is formed are arranged a first optically anisotropic element 2 consisting of stretched polymeric carbonate films 13 (Δnd: about 268 nm), 14 (Δnd: about 98 nm) each formed of a uniaxially stretched polycarbonate film and a polarizer 1 while on the side of the second substrate 8, opposite to the side on which the reflective and transparent electrodes 6, 7 are formed are arranged a second optically anisotropic element 9 consisting of the liquid crystal film 1 produced in Example 5 and a stretched polymeric carbonate film 16 (Δnd: about 272 nm) formed of a uniaxially stretched polycarbonate film and a polarizer 10. On the rear side of the polarizer 10 is arranged a backlight 11.

The liquid crystal cell 12 used in this example was produced using ZLI-1695 (manufactured by Merck Ltd) as a liquid crystalline material. The liquid crystal layer thicknesses in the reflective electrode region 6 (reflective display part) and the transparent electrode region 7 (transmissive display part) were set to 2.4 μm and 4.8 μm, respectively. The pre-tilt angle of the liquid crystal layer at both of the substrate interfaces was 2 degrees. The Δnds of the liquid crystal cell in the reflective display part and transmissive display part are approximately 150 nm and 300 nm, respectively.

The polarizers 1 and 10 arranged on the viewer's side of the liquid crystal cell 12 and on the opposite side thereof were "SQW-862" (thickness: about 180 μm) manufactured by Sumitomo Chemical Industry Co., Ltd.

The absorption axes of the polarizers 1, 10, the slow axes of the polymeric stretched films 13, 14 and 16, the pre-tilt direction of the cell 12 at both of the interfaces, and the tilt direction of the liquid crystal film 1 were oriented as shown in FIG. 10.

When the display device produced above is compared with that wherein a polycarbonate 15 (Δnd: about 137 nm) was used instead of the optical film 1, it was confirmed that the viewing angle characteristics was enlarged by 20 degrees due to the use of the optical film 1 with a hybrid nematic structure.

APPLICABILITY IN THE INDUSTRY

An optical film with excellent retainability of the liquid crystal orientation and excellent mechanical strength can be provided by polymerizing the novel dioxetane compound of the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A dioxetane compound represented by formula (1) below:

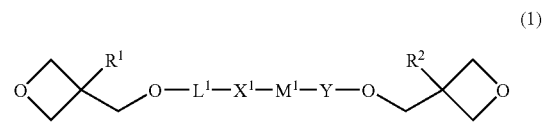

(1)

wherein $R^1$ and $R^2$ are each independently hydrogen, methyl, or ethyl, $L^1$ denotes —$(CH_2)_n$— wherein n is an integer of 1 to 12, $X^1$ denotes a single bond, —O—, —O—CO— or —CO—O—, Y denotes a single bond or —CO—, $M^1$ is represented by formula (2) or (3) below wherein $P^1$ and $P^3$ are each independently a group selected from the group consisting of those represented by formula (4) below, and $P^2$ is a group selected from the group consisting of those represented by formula (5) below, and $L^2$ and $L^3$ are each denotes a single bond, —CH═CH—, —C≡C—, —O—, —O—CO—, or —CO—O—:

  (2)

  (3)

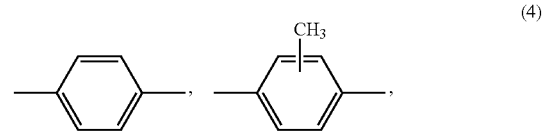  (4)

-continued

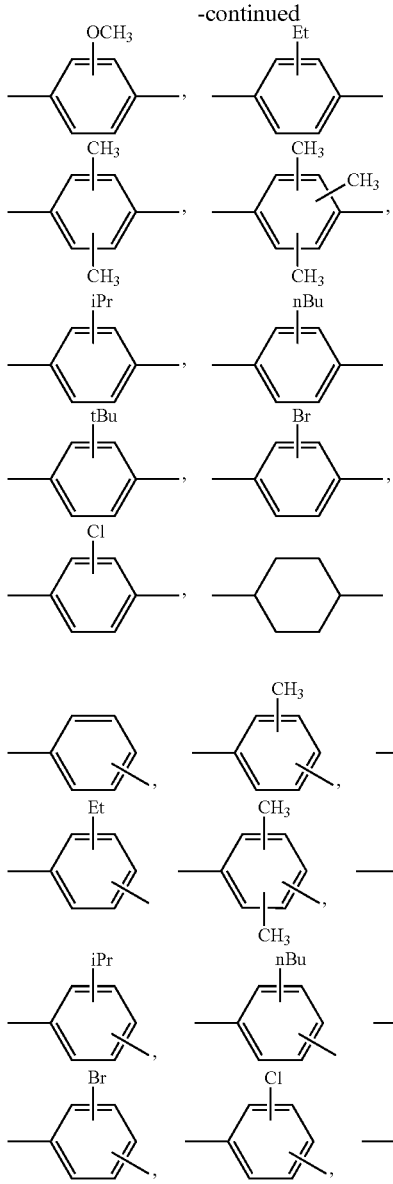

2. The dioxetane compound according to claim 1 wherein in formula (1) $L^1$ is —$(CH_2)_2$—, —$(CH_2)_4$—, or —$(CH_2)_6$—, and Y is a single bond.

3. A cationically polymerizable composition comprising a dioxetane compound represented by formula (1)

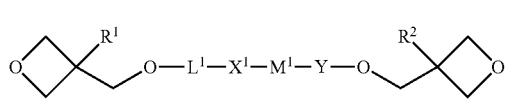
(1)

wherein $R^1$ and $R^2$ are each independently hydrogen, methyl, or ethyl, $L^1$ denotes —$(CH_2)_n$— wherein n is an integer of 1 to 12, $X^1$ denotes a single bond, —O—, —O—CO— or —CO—O—, Y denotes a single bond or —CO—, $M^1$ is represented by formula (2) or (3) below wherein $P^1$ and $P^3$ are each independently a group selected from the group consisting of those represented by formula (4) below, and $P^2$ is a group selected from the group consisting of those represented by formula (5) below, and $L^2$ and $L^3$ are each denotes a single bond, —CH=CH—, —C≡C—, —O—, —O—CO—, or —CO—O—;

—$P^1$—$L^2$—$P^2$—$L^3$—$P^3$— (2)

—$P^1$—$L^2$—$P^3$— (3)

(4)

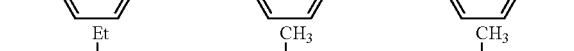
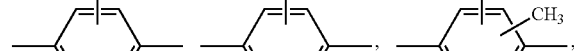
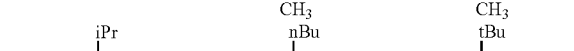
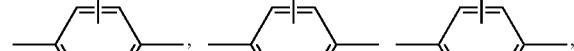
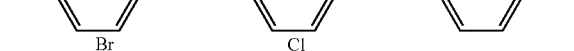
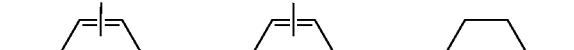
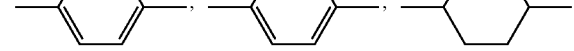

(5)

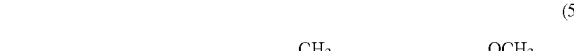
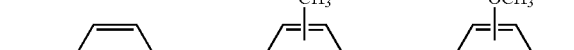
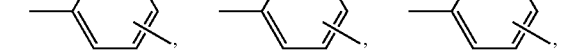
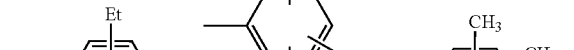
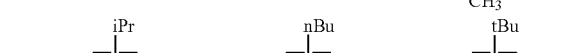
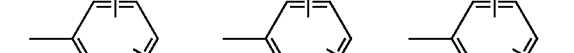
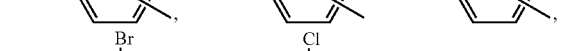

and a compound having a cationically polymerizable group, excluding the compound represented by formula (1).

4. The cationically polymerizable composition according to claim 3 wherein the composition contains at least 5 percent by mass or more of a dioxetane compound represented by formula (1).

5. The cationically polymerizable composition according to claim 3 wherein the compound having a cationically polymerizable group is a compound exhibiting liquid crystallinity.

6. The cationically polymerizable composition according to claim 5 wherein the compound exhibiting liquid crystallinity is an oligomer or a polymer.

7. The cationically polymerizable composition according to claim 3 wherein the composition contains a photo cation generator and/or a thermal cation generator.

8. An optical film produced by polymerizing the cationically polymerizable composition according to claim 3.

9. A liquid crystal display equipped with the optical film according to claim 8.

10. An optical film produced by polymerizing the cationically polymerizable composition according to claim 4.

11. An optical film produced by polymerizing the cationically polymerizable composition according to claim 5.

12. An optical film produced by polymerizing the cationically polymerizable composition according to claim 6.

13. An optical film produced by polymerizing the cationically polymerizable composition according to claim 7.

* * * * *